(12) United States Patent
Seifer et al.

(10) Patent No.: US 12,329,775 B2
(45) Date of Patent: Jun. 17, 2025

(54) COMPOSITION AND METHOD FOR TREATING HEARING LOSS

(71) Applicant: Soundbites Public Benefit Corporation, Ann Arbor, MI (US)

(72) Inventors: Barry S. Seifer, Ann Arbor, MI (US); Louise A. Minor, Trinidad, CA (US); Richard A. Detweiler, West Linn, OR (US)

(73) Assignee: Soundbites Public Benefit Corporation, Ann Arbor, MI (US)

( * ) Notice: Subject to any disclaimer, the term of this patent is extended or adjusted under 35 U.S.C. 154(b) by 0 days.

(21) Appl. No.: 18/799,983

(22) Filed: Aug. 9, 2024

(65) Prior Publication Data

US 2025/0057875 A1    Feb. 20, 2025

Related U.S. Application Data

(60) Provisional application No. 63/557,066, filed on Feb. 23, 2024, provisional application No. 63/532,714, filed on Aug. 15, 2023.

(51) Int. Cl.
| | |
|---|---|
| *A61K 33/06* | (2006.01) |
| *A61K 9/00* | (2006.01) |
| *A61K 31/015* | (2006.01) |
| *A61K 31/355* | (2006.01) |
| *A61K 31/375* | (2006.01) |
| *A61P 27/16* | (2006.01) |

(52) U.S. Cl.
CPC ............ *A61K 33/06* (2013.01); *A61K 9/0053* (2013.01); *A61K 31/015* (2013.01); *A61K 31/355* (2013.01); *A61K 31/375* (2013.01); *A61P 27/16* (2018.01)

(58) Field of Classification Search
CPC .... A61K 33/06; A61K 9/0053; A61K 31/015; A61K 31/355; A61K 31/375; A61P 27/16
See application file for complete search history.

(56) References Cited

U.S. PATENT DOCUMENTS

| | | | |
|---|---|---|---|
| 5,310,554 A | 5/1994 | Haigh | |
| 5,977,073 A | 11/1999 | Khaled | |
| 7,951,845 B2 | 5/2011 | Miller et al. | |
| 8,652,518 B2 | 2/2014 | Finley | |
| 9,308,189 B2 | 4/2016 | Miller | |
| 9,579,346 B2 | 2/2017 | McGrath | |
| 10,238,599 B2 * | 3/2019 | Miller | A61K 9/0046 |
| 2020/0316065 A1 | 10/2020 | Nakai et al. | |
| 2022/0279831 A1 | 9/2022 | Perrin et al. | |

FOREIGN PATENT DOCUMENTS

WO    2025/038498 A2    2/2025

OTHER PUBLICATIONS

Hsu, Ching-Yun; Wang, Pei-Wen; Alalaiwe, Ahmed; Lin, Zih-Chan; Fang, Jia-You. Use of Lipid Nanocarriers to Improve Oral Delivery of Vitamins. Nutrients, 11, 68, 1-30. (Year: 2019).*
"A novel micronutrient-based strategy to prevent hearing impairments: test and road to market for age-related hearing loss and preservation of residual hearing," retrieved from the internet, <https://cordis.europa.eu/project/id/304925,> Feb. 23, 2022.
Alvarado, J.C., et al., "Oral Antioxidant Vitamins and Magnesium Limit Noise-Induced Hearing Loss by Promoting Sensory Hair Cell Survival: Role of Antioxidant Enzymes and Apoptosis Genes," Antioxidants, 9(12):1177 (2020).
Curhan, et al. "Carotenoids, Vitamin A, Vitamin C, Vitamin E, and Folate and Risk of Self-reported Hearing Loss in Women," The American Journal of Clinical Nutrition, 102(5): 1167-1175 (2015).
Eisenhut, M., "Evidence Supporting the Hypothesis that Inflammation-Induced Vasospasm is Involved in the Pathogenesis of Acquired Sensorineural Hearing Loss," Int J Otolaryngol. 2019:4367240 (2019).
Evans, P., et al., "Free Radicals and Hearing. Cause, Consequence, and Criteria," Annals of the New York Academy of Sciences, 884:19-40 (1999).
Final Report Summary—"A Novel Micronutrient-based Strategy to Prevent Hearing Impairments: Test and Road to Market for Age-related Hearing Loss and Preservation of Residual Hearing," Prohearing Consortium, available from cordis.europa.eu/project/id/304925/reporting/it, May 30, 2024.
Forge, A., et al., "Aminoglycoside Antibiotics," Audiol. Neurootol., 5:3-22 (2000).
Fujimoto, C., et al., "Mitochondria-Targeted Antioxidants for Treatment of Hearing Loss: A Systematic Review," Antioxidants 8(4) (2019).
International Search Report from International Application No. PCT/US2024/041837, dated: Nov. 18, 2024.
Jiang, F., et al. "Association between hearing aid use and all-cause and cause-specific dementia: an analysis of the UK Biobank cohort." The Lancet Public Health 8.5:e329-e338 (2023).
Kaya, et al., "Vitamins A, C, and E and Selenium in the Treatment of Idiopathic Sudden Sensorineural Hearing Loss," Eur. Arch. Otorhinolaryngol, 272(5): 1119-1125 (2015).
Le Prell, C.G., "Free Radical Scavengers Vitamins A, C, and E Plus Magnesium Reduce Noise Trauma," Free Radic Biol Med, 42(9):1454-63 (2007).
Le Prell, C.G., et al., "Evidence of Hearing Loss in a 'Normally-hearing' College-student Population," Int J Audiol., 50 (Suppl 1):S21-S31 (2011).

(Continued)

Primary Examiner — Jessica Worsham
(74) Attorney, Agent, or Firm — Morse, Barnes-Brown & Pendleton, P.C.; Sean D. Detweiler, Esq.

(57) ABSTRACT

A composition for treating hearing loss, and more particularly to restoring a level of hearing or reducing the likelihood of developing hearing loss in a subject. In addition, a composition for reducing the severity or risk of developing dementia or Alzheimer's disease, along with methods for using this composition are also disclosed.

20 Claims, 23 Drawing Sheets

(56) References Cited

OTHER PUBLICATIONS

Le Prell, et al., "Increased Vitamin Plasma Levels in Swedish Military Personnel Treated with Nutrients Prior to Automatic Weapon Training," Noise Health, 13(55):432-443 (2011).
Livingston G., et al., "Dementia Prevention, Intervention, and Care: 2020 Report of the Lancet Commission," Lancet, 10248:413-446 (2020).
Lobo, V., et al. "Free Radicals, Antioxidants and Functional Foods: Impact on Human Health," Pharmacognosy Reviews, 4(8): 118-26 (2010).
Minami, S. B., et al., "Calcineurin Activation Contributes to Noise-induced Hearing Loss," Journal of Neuroscience Research, 78 (3):383-392 (2004).
Niki, E., "Interaction of Ascorbate and Alpha-tocopherol," Annals of the New York Academy of Sciences, 498:186-199 (1987).
Niki, E., "Lipid Antioxidants: How They May Act in Biological Systems," The British Journal of Cancer, Supplement 8: 153-157 (1987).
Ohinata, Y., "Protection from Noise-induced Lipid Peroxidation and Hair Cell Loss in the Cochlea," Brain Research, 966 (2): 265-273 (2003).
Op de Beeck, K., "Apoptosis in Acquired and Genetic Hearing Impairment: The Programmed Death of the Hair Cell,"Hear Res. 281(1-2):18-27 (2011).
O'Sullivan, J.D.B., "Mitochondrial Form and Function in Hair Cells," Hear Res., 428:108660 (2023).
Schafer, F. Q., et al., "Comparing Beta-carotene, Vitamin E and Nitric Oxide as Membrane Antioxidants," Biological Chemistry, 383(3-4): 671-681 (2002).

Scheper, V., et al. "Randomized Placebo-controlled Clinical Trial Investigating the Effect of Antioxidants and a Vasodilator on Overall Safety and Residual Hearing Preservation in Cochlear Implant Patients," Trials , 21(1): 643 (2020).
Sha, S.H., "Aspirin to Prevent Gentamicin-Induced Hearing Loss," New Engl. J. Med 354: 1856-1857 (2006).
Shoji, F., et al., "Glial cell line-derived neurotrophic factor has a dose dependent influence on noise-induced hearing loss in the guinea pig cochlea," Hearing Research, 142 (1-2): 41-55 (2000).
Shoji, F., et al., "Differential protective effects of neurotrophins in the attenuation of noise-induced hair cell loss," Hearing Research, 146 (1-2): 134-142 (2000).
Takemura, K., et al., "Direct Inner Ear Infusion of Dexamethasone Attenuates Noise-induced Trauma in Guinea Pig," Hearing Research, 196 (1-2): 58-68 (2004).
Tanna, R.J., et al., "Sensorineural Hearing Loss," StatPearls [Internet]. Treasure Island (FL): StatPearls Publishing, (2023).
Yamashita, D., et al., "AIF and EndoG in Noise-induced Hearing Loss," Neuroreport, 15 (18): 2719-2722 (2004).
Yamashita, D., et al., "Delayed Production of Free Radicals Following Noise Exposure," Brain Research, 1019 (1-2): 201-209 (2004).
Yamasoba, .T, et al., "Role of Glutathione in Protection Against Noise-induced Hearing Loss," Brain Res., 784 (1-2):82-90 (1998).
Yamasoba, T., et al., "Influence of intense sound exposure on glutathione synthesis in the cochlea," Brain Research, 804(1): 72-78 (1998).
Kempfle, J.S. et al., "Experimental drugs for the prevention or treatment of sensorineural hearing loss", Expert Opinion on Investigational Drugs, 32:7, 643-654, Aug. 20, 2023.

\* cited by examiner

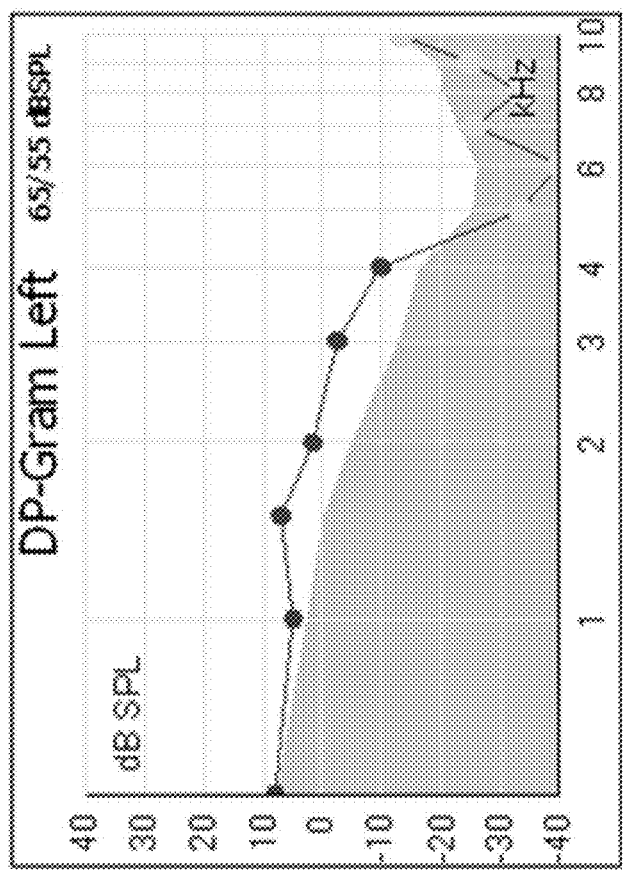
Fig. 1A
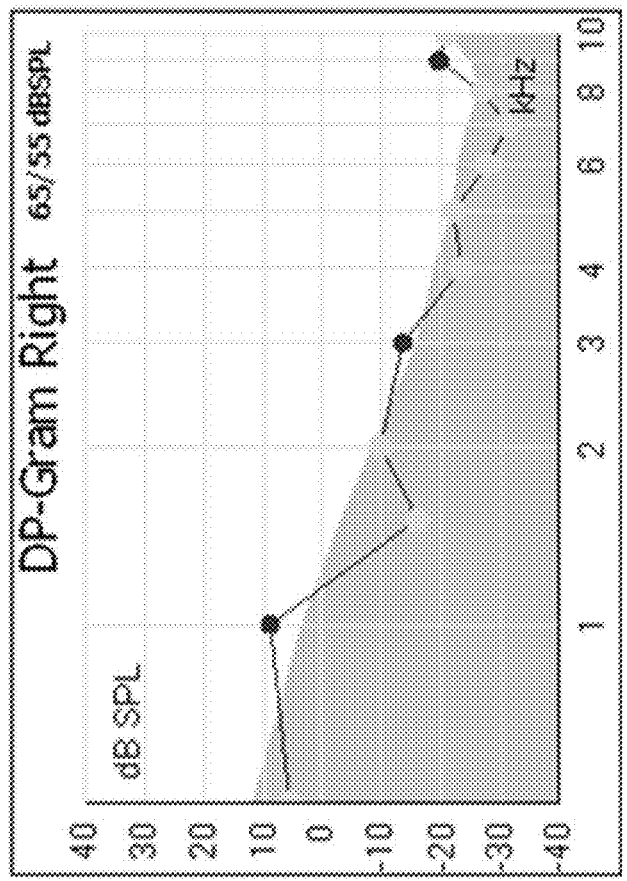
Fig. 1B
Figures 1A-1B

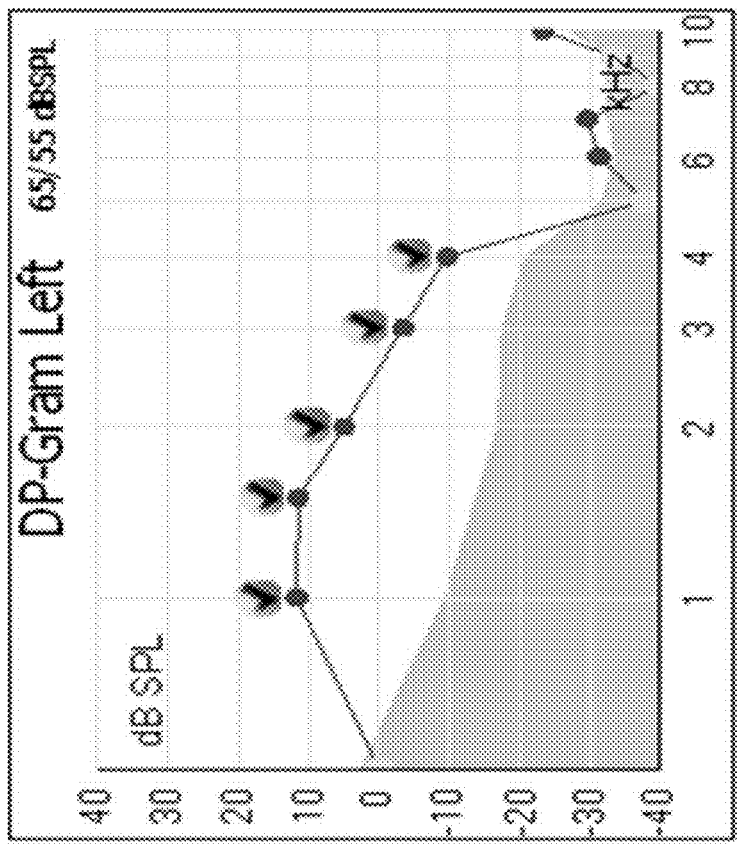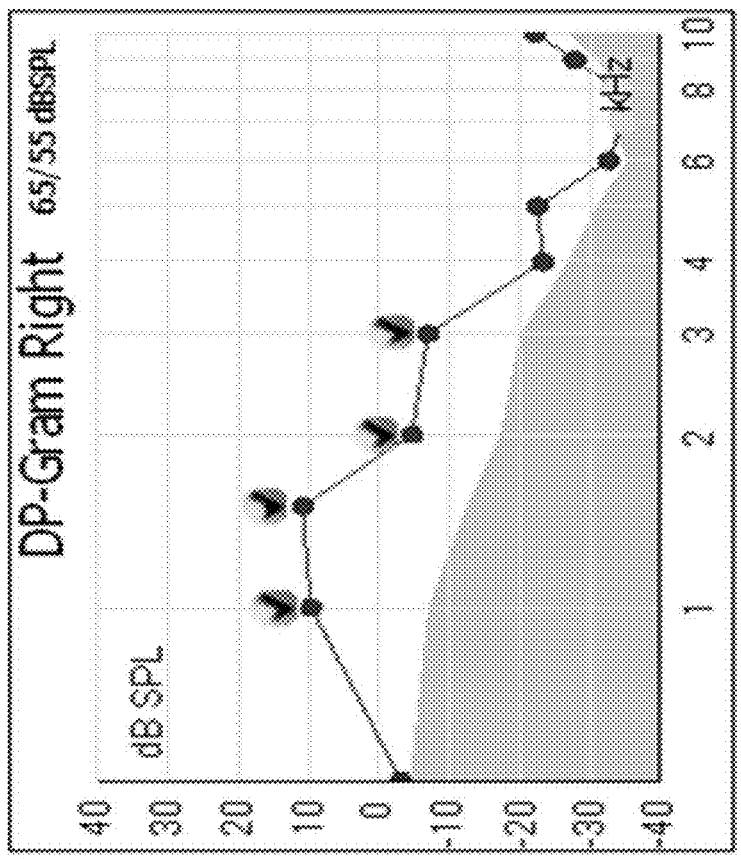
Fig. 2B
Fig. 2A
Figures 2A-2B

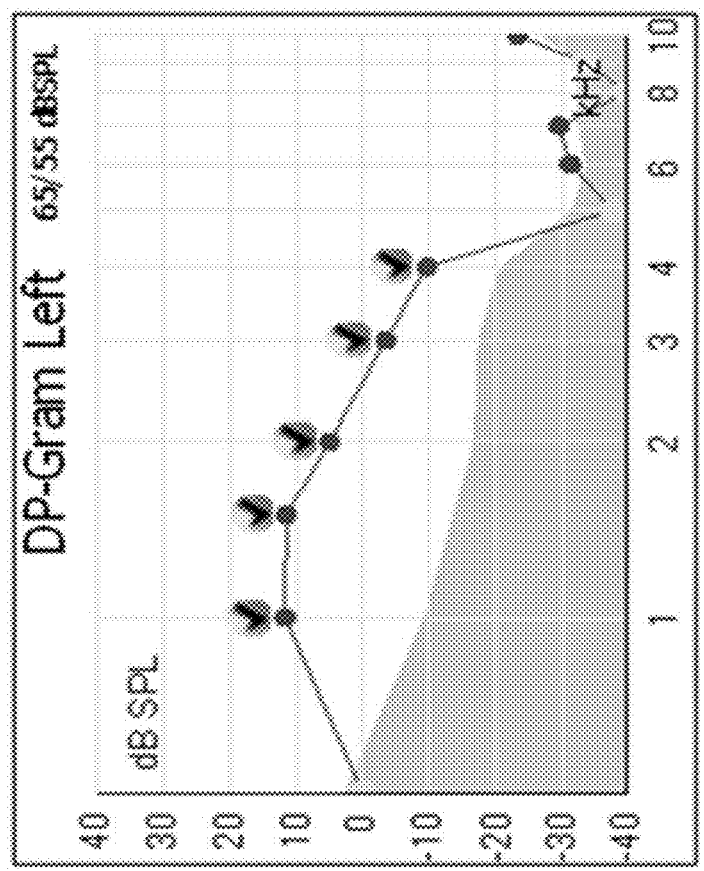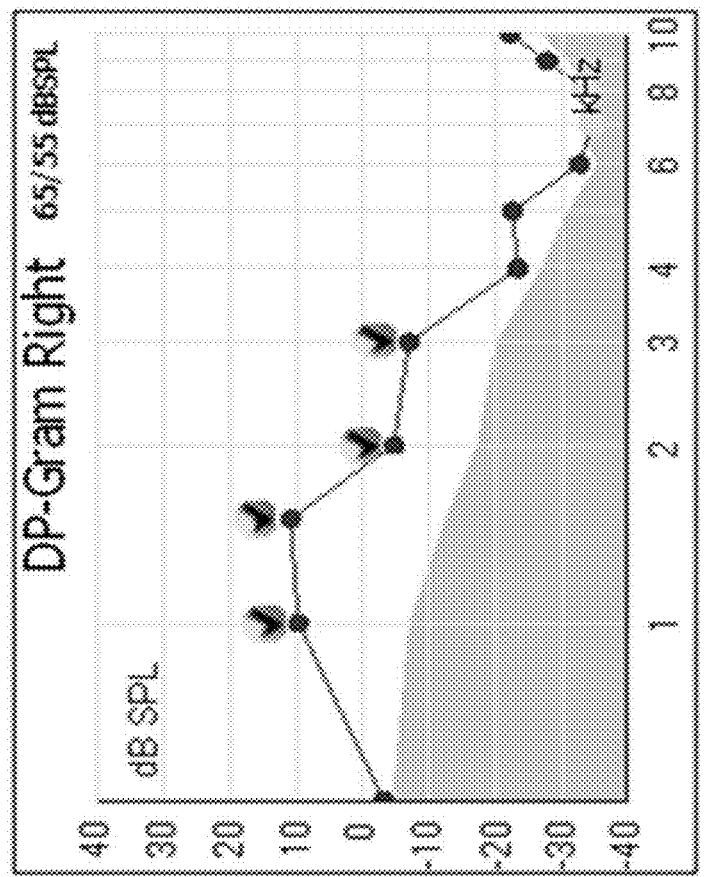
Fig. 3A
Fig. 3B
Figures 3A-3B

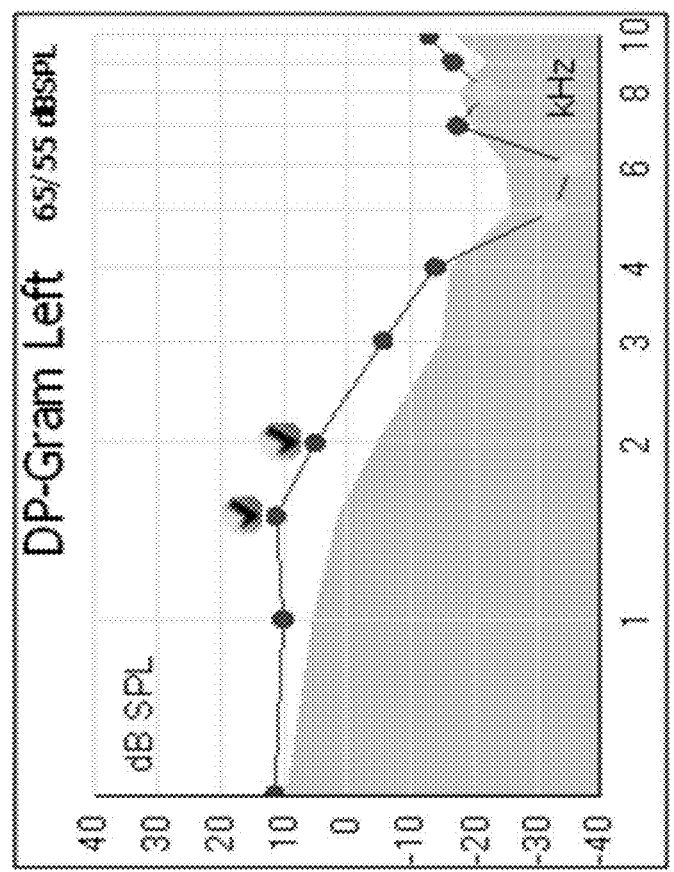
Fig. 4A
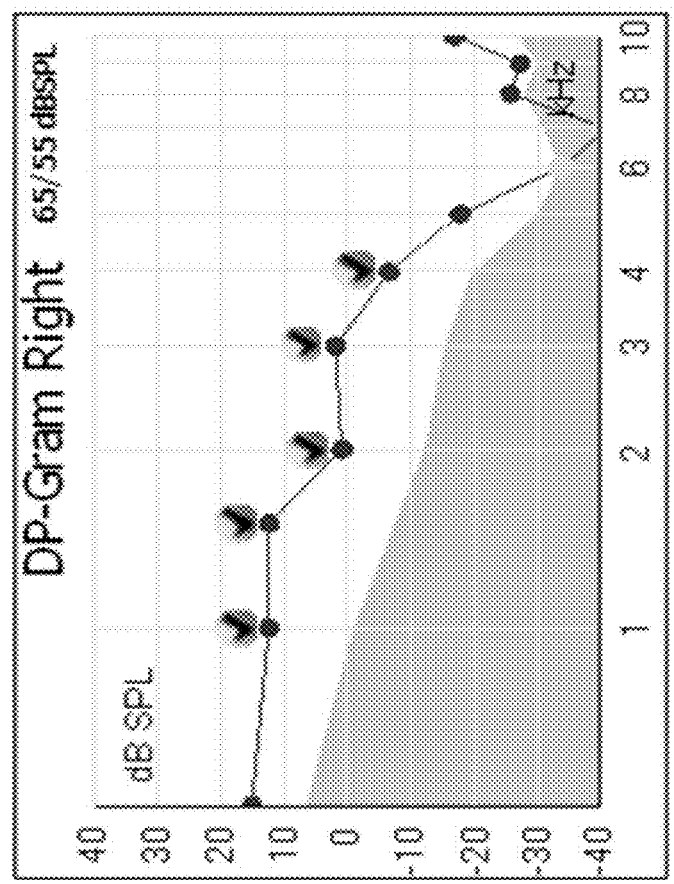
Fig. 4B
Figures 4A-4B

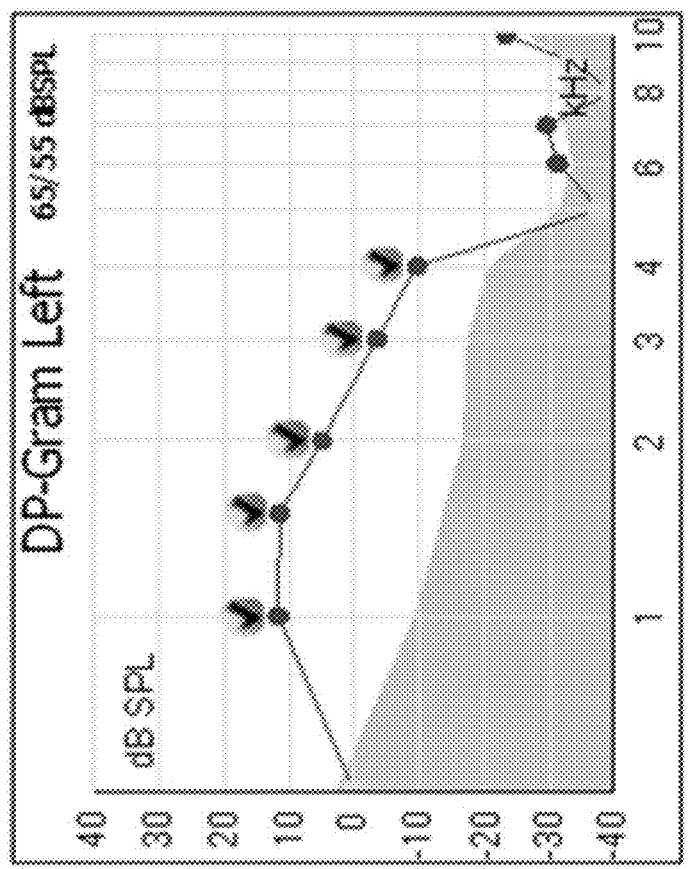
Fig. 5B
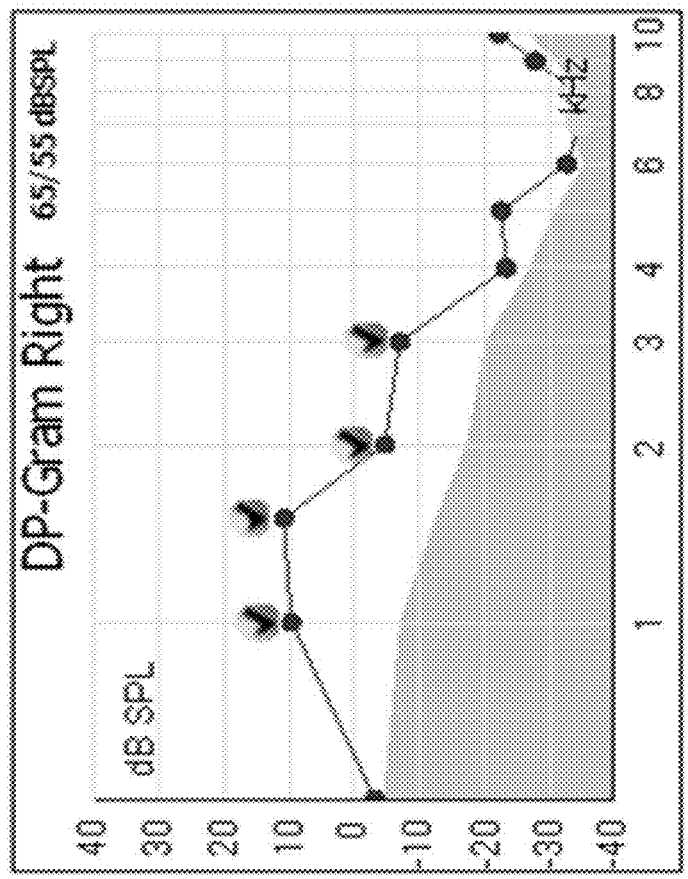
Fig. 5A
Figures 5A-5B

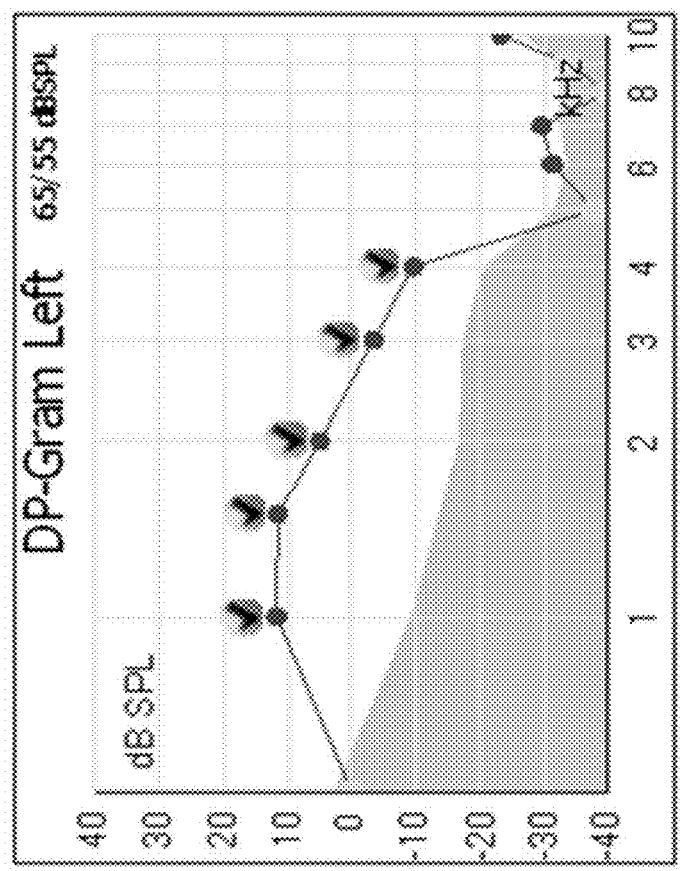
Fig. 6A
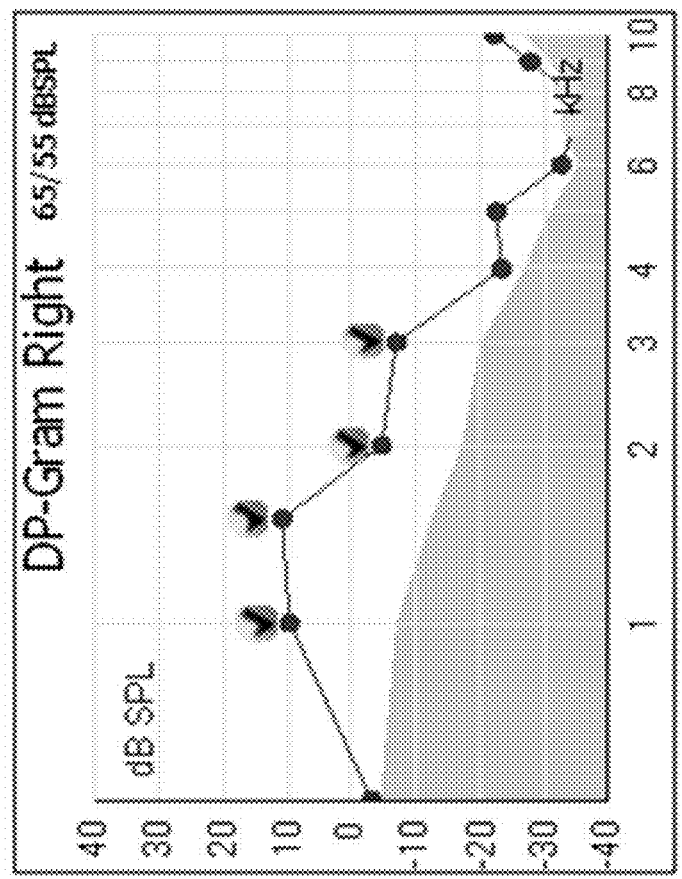
Fig. 6B
Figures 6A-6B

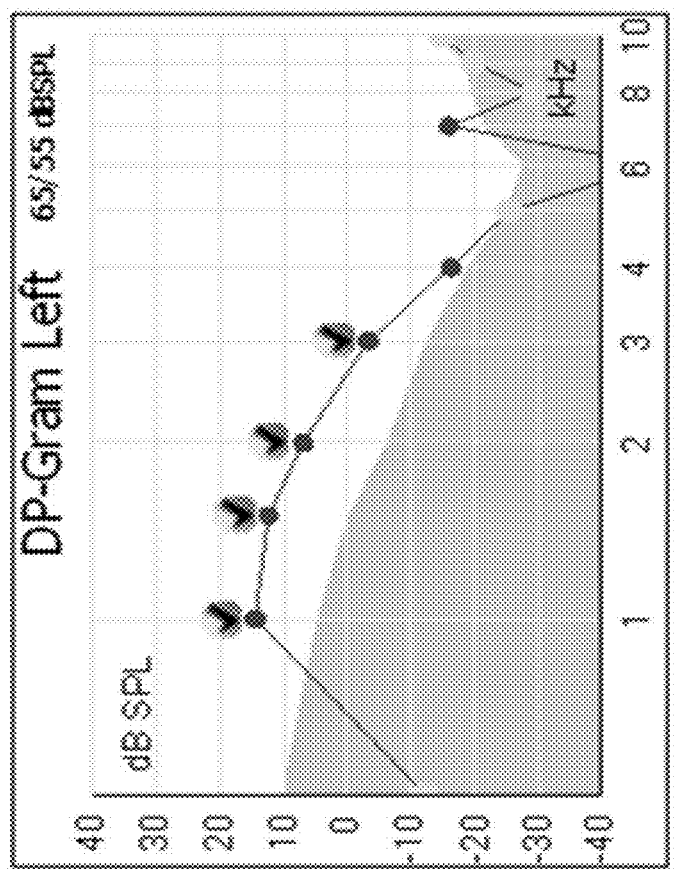
Fig. 7B
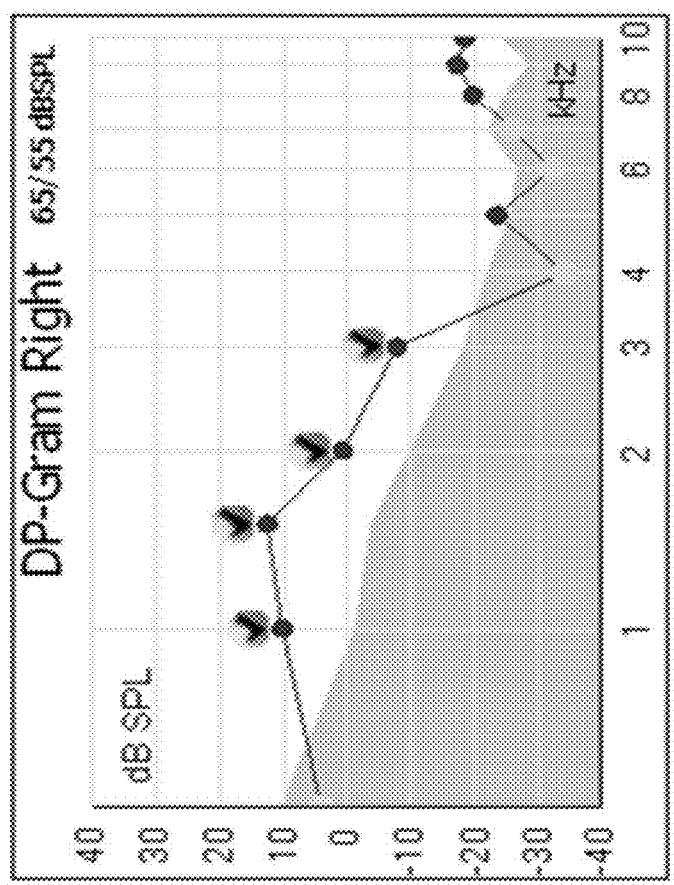
Fig. 7A
Figures 7A-7B

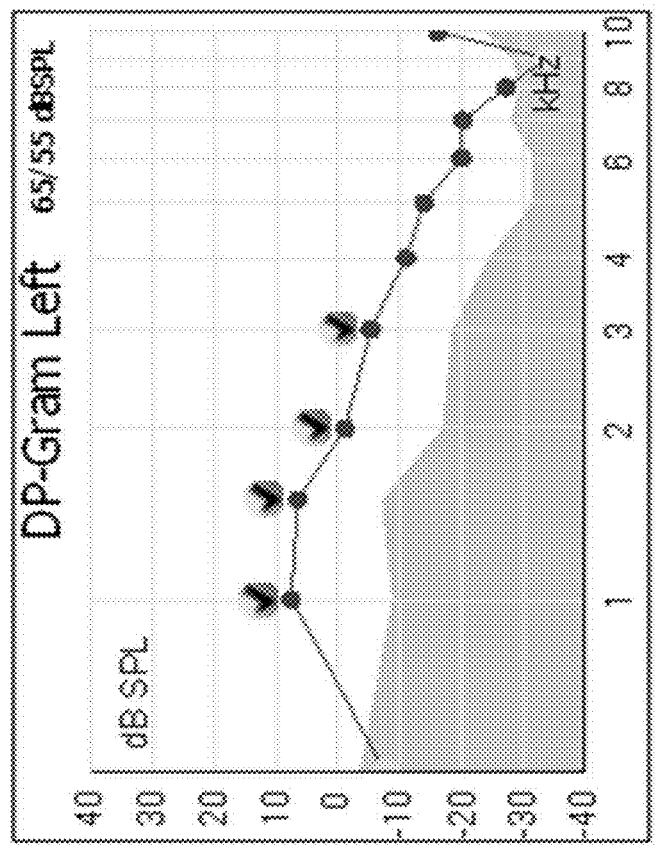
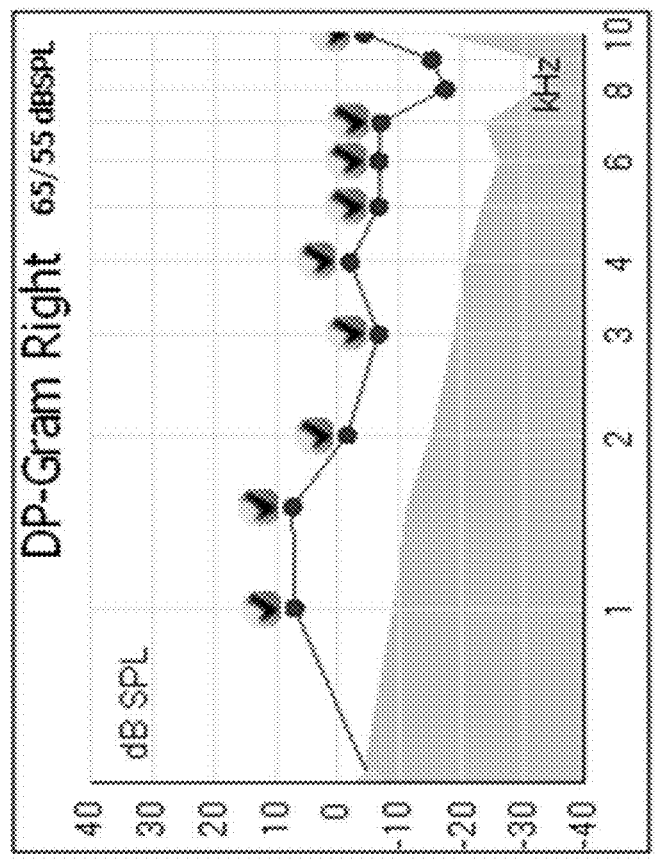
Fig. 8A
Fig. 8B
Figures 8A-8B

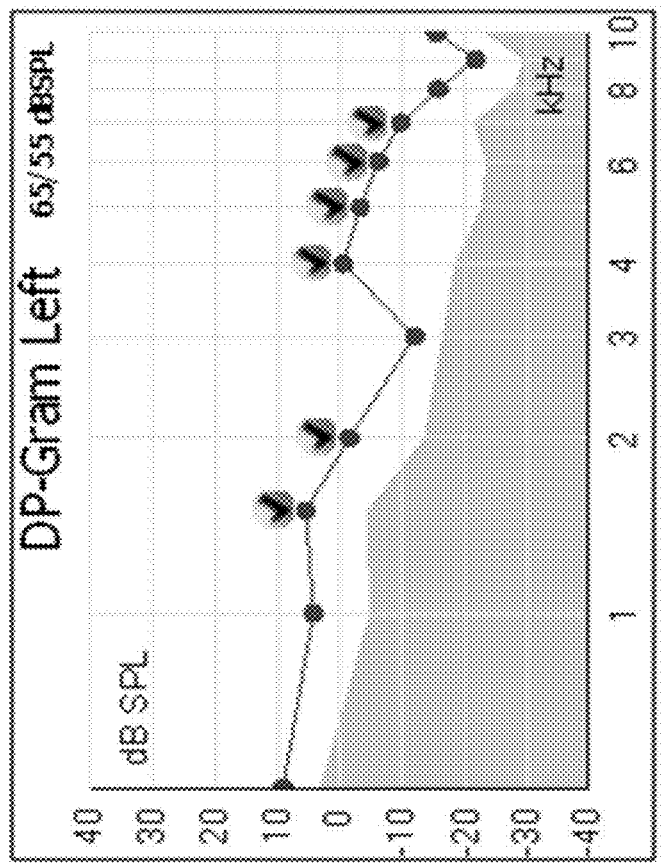
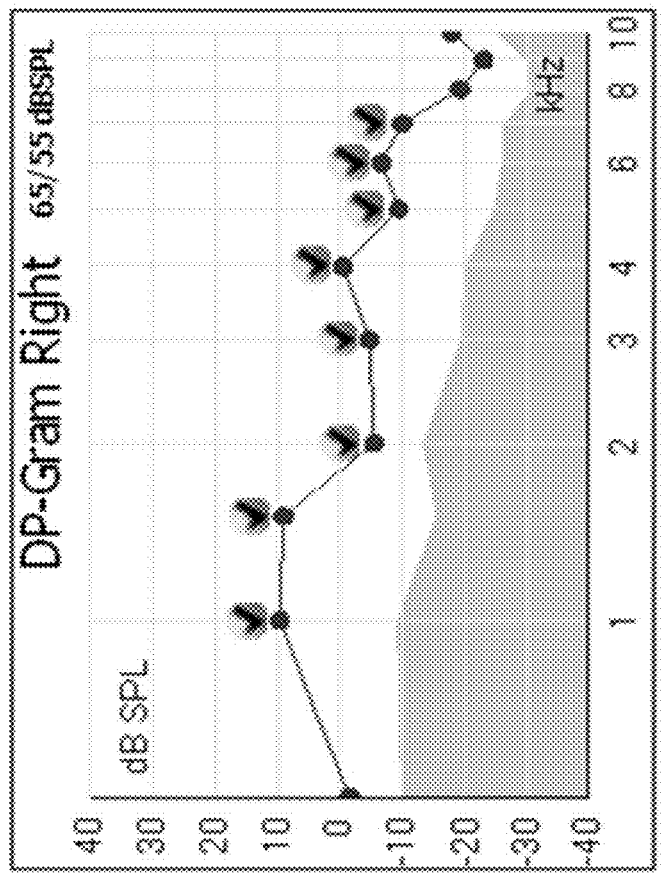
Fig. 9A-9B
Figures 9A-9B

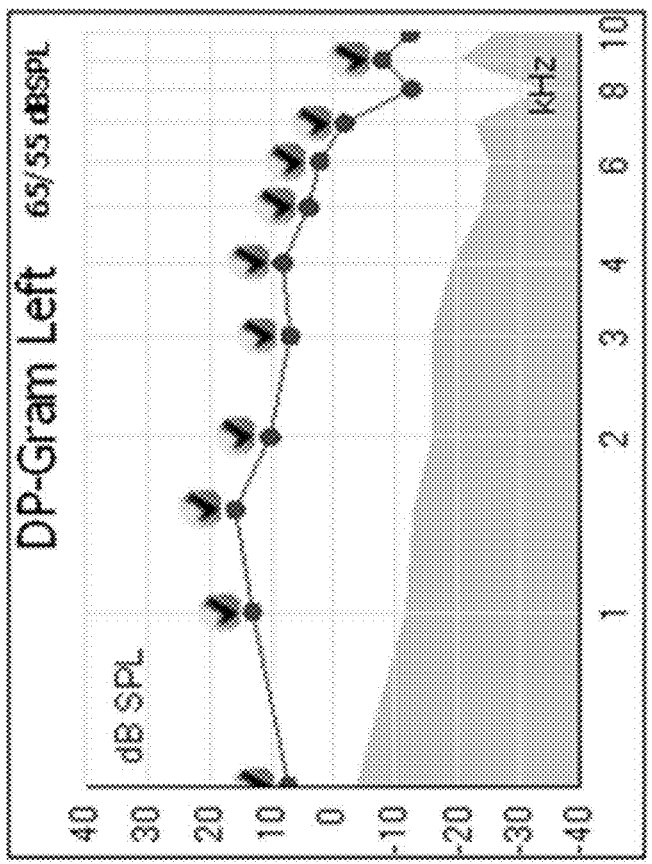
Fig. 10B
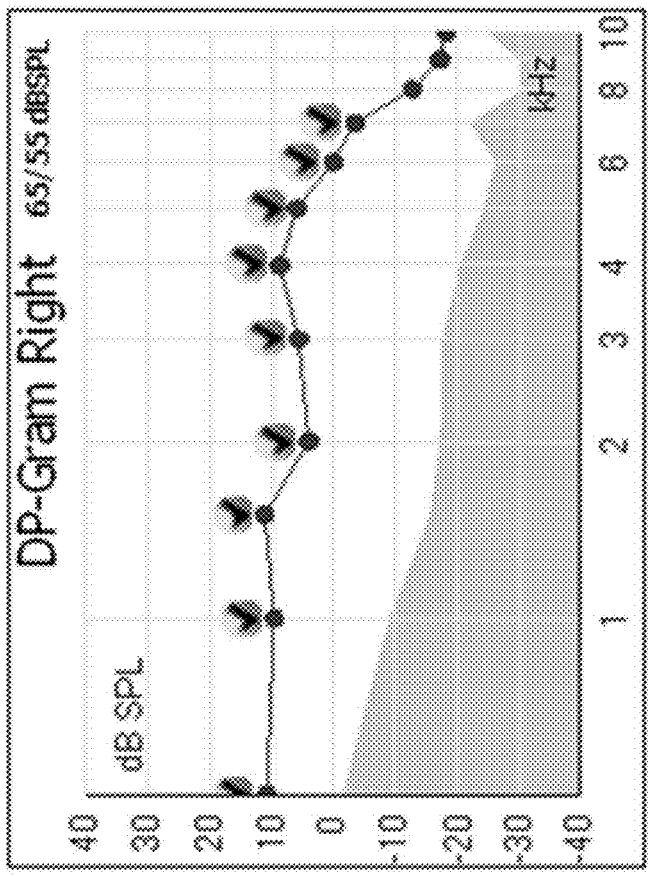
Fig. 10A
Figures 10A-10B

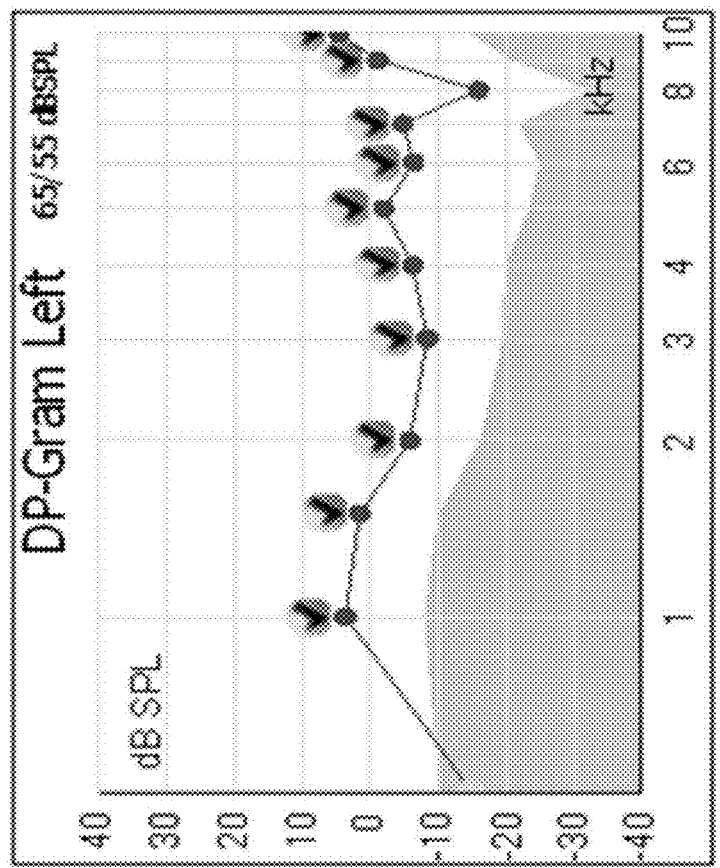
Fig. 12A
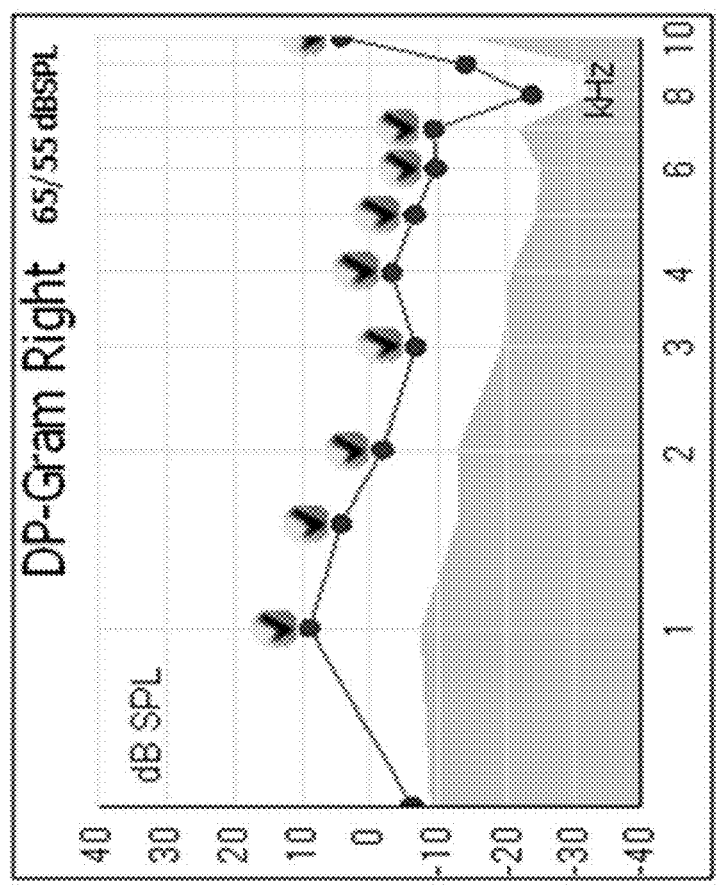
Fig. 12B
Figures 12A-12B

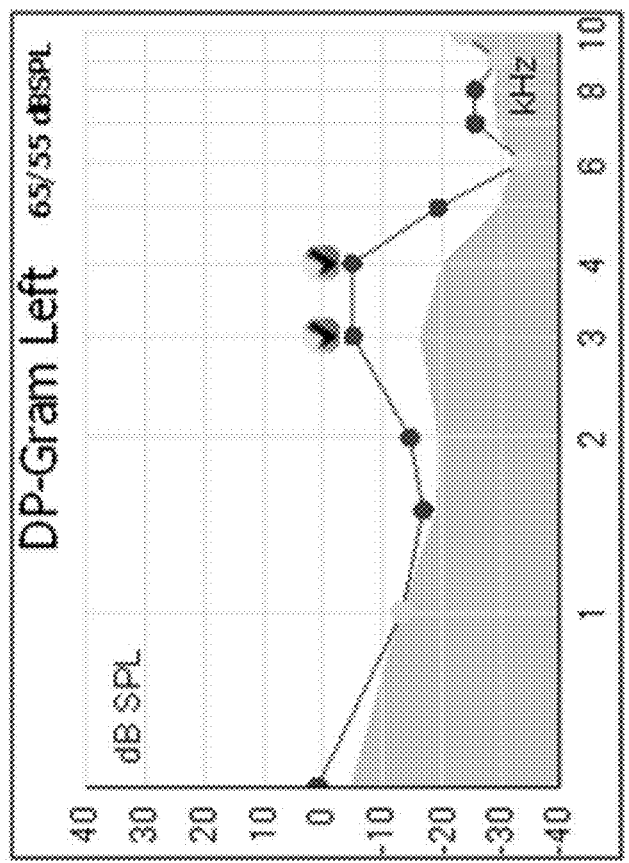
Fig. 17B
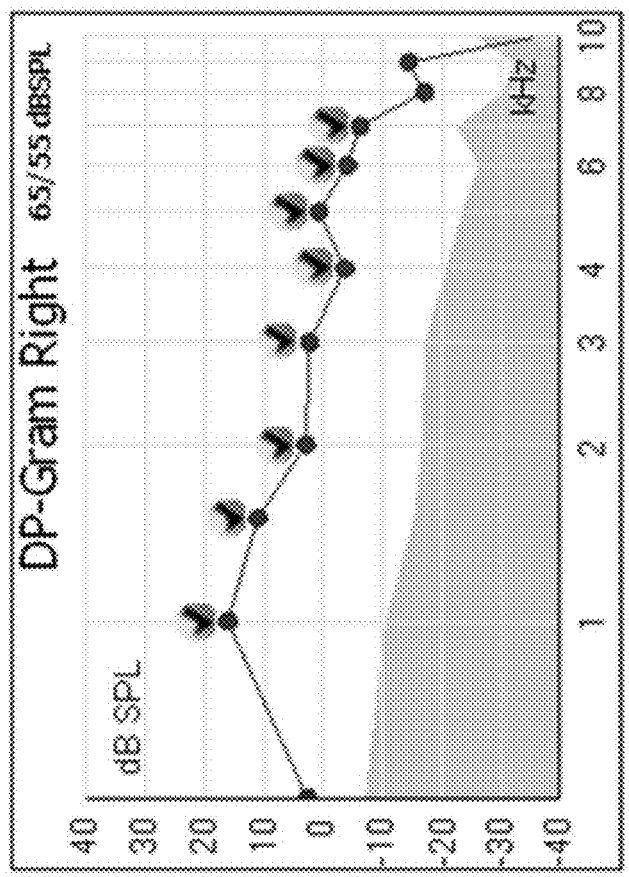
Fig. 17A
Figures 17A-17B

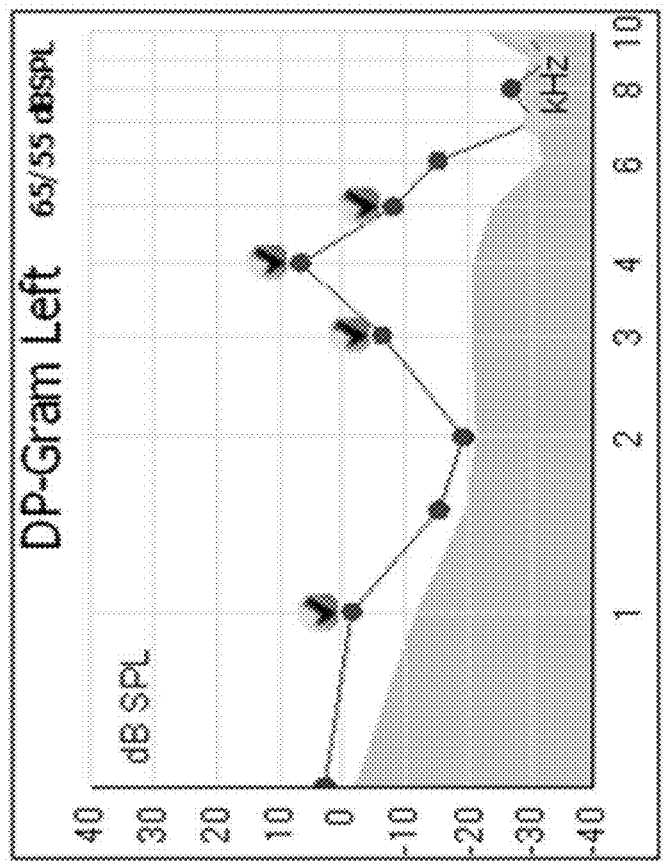
Fig. 18B
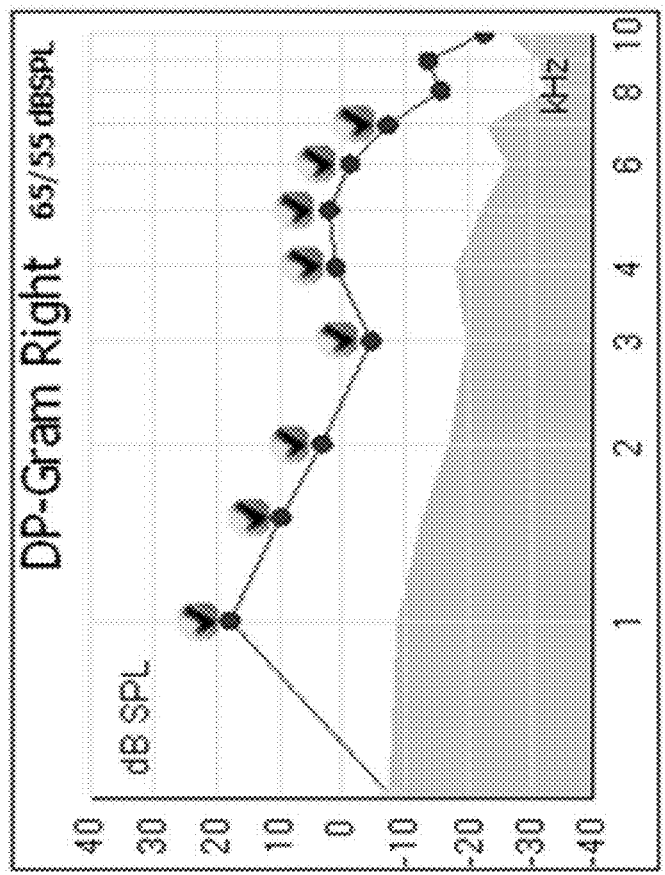
Fig. 18A
Figures 18A-18B

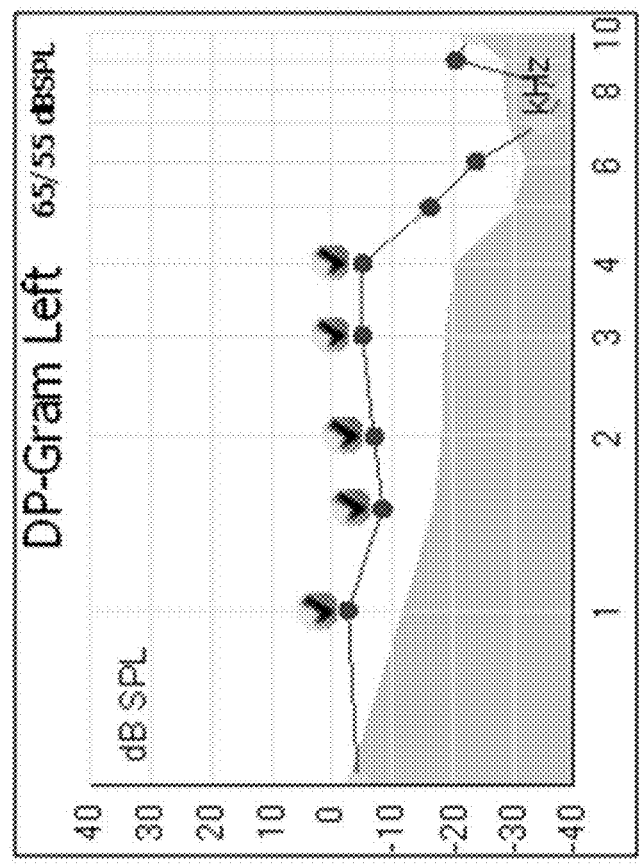
Fig. 19B
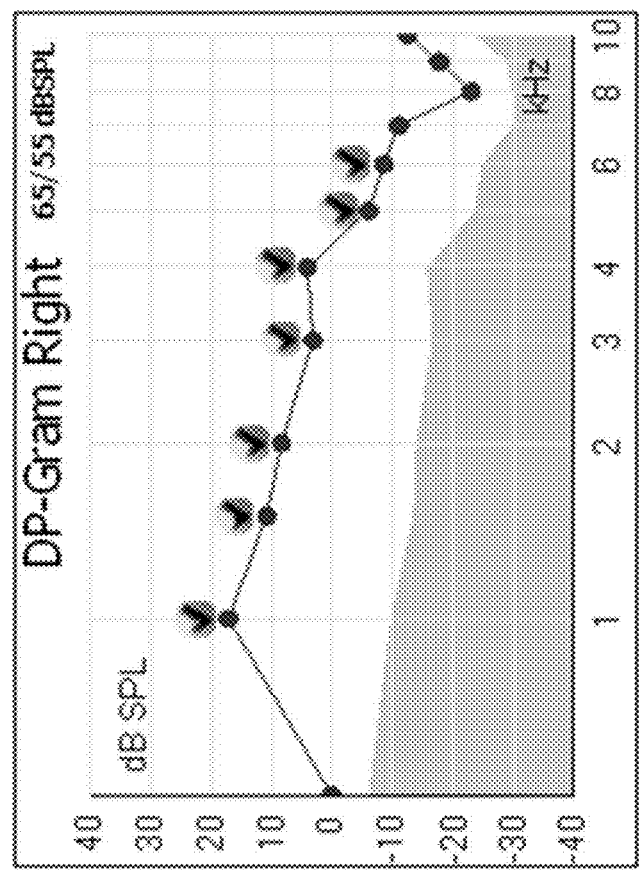
Fig. 19A
Figures 19A-19B

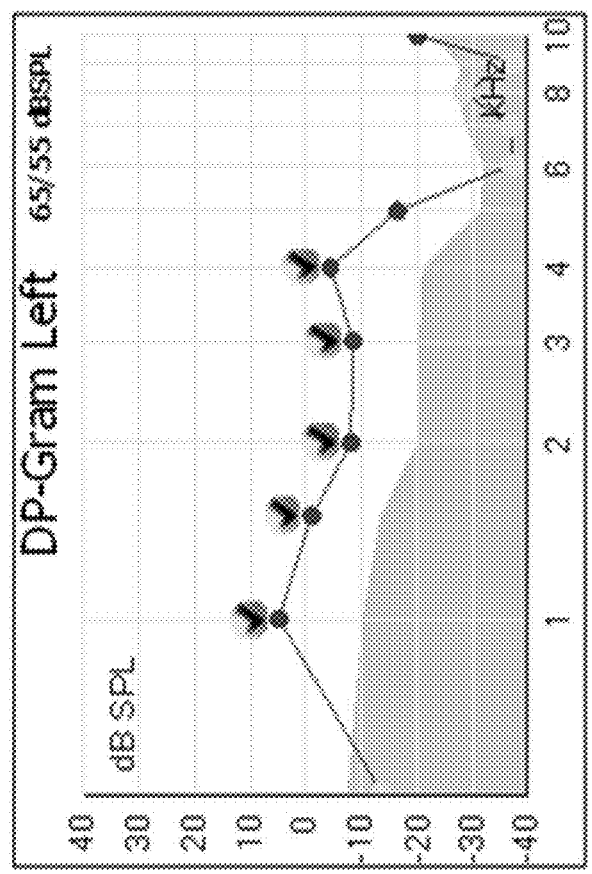
Fig. 20B
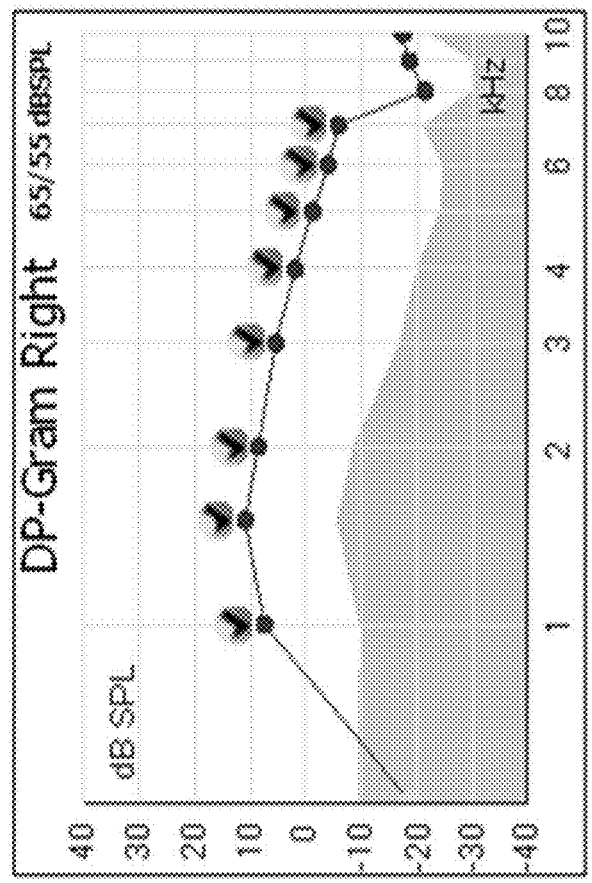
Fig. 20A
Figures 20A-20B

COMPOSITION AND METHOD FOR TREATING HEARING LOSS

CROSS REFERENCE TO RELATED APPLICATIONS

This application claims priority to, and the benefit of, U.S. Provisional Application No. 63/532,714, filed Aug. 15, 2023, and Provisional Application No. 63/557,066, filed Feb. 23, 2024. The entire teachings of the above applications are incorporated herein by reference in their entireties.

BACKGROUND OF THE INVENTION

Hearing loss affects nearly 1.5 billion people throughout the world, or nearly 20% of the world's human population. This number is estimated to reach nearly 2.5 billion people by the year 2050. Hearing loss can negatively impact the affected individual socially, cognitively, emotionally, and educationally; in addition, hearing loss can have stark economic consequences for both the affected individual and for society as a whole. In fact, the World Health Organization estimates that the aggregate global cost of unresolved hearing loss totals 980 billion U.S. dollars annually.

Due to the widespread nature of hearing loss, along with its high costs for affected individuals and society, it is not surprising that considerable time and capital have been invested in exploring the etiologies and possible treatments for hearing loss. Despite this immense cumulative investment, to date methods for preventing or treating hearing loss have seen only limited success, with solutions ranging from earplugs or earmuffs for preventing hearing loss to amplifying sounds in the ear, such as by the use of hearing aids.

In a 2011 research study conducted by Le Prell et al., (*Noise Health*, 13.55 (2011): 432-443), the group sought to determine if administration of vitamin A, vitamin C, vitamin E, and magnesium in a weight ratio of approximately 1:28:17:108 would reduce noise-induced threshold shift in military personnel exposed to gunfire. While some of the most sensitive subjects demonstrated reduced noise-induced threshold shift when pre-treated with the test composition compared to placebo, there was not a statistically significant protective effect. Moreover, the compounds were delivered in the form of tablets, with a total of 6 tablets required daily to obtain the recommended dose.

In a 2015 study of the treatment of idiopathic sudden sensorineural hearing loss (Kaya et al., *Eur. Arch. Otorhinolaryngol*, 272 (2015): 1119-1125), the effects of vitamin A, vitamin C, vitamin E and selenium on ameliorating idiopathic sudden sensorineural hearing loss was investigated. While the treated group demonstrated improved hearing, the treatment regimen also comprised administration of methylprednisolone, Rheo-macrodex®, Vasterel®, as well as hyperbaric oxygen. These treatments are not without their side-effects, and Kaya et al. note that hyperbaric oxygen treatments can "increase free radical levels in the cochlea and potentiate the damage to hair cells," while steroid treatments have been known to cause hepatopathy and leukocytosis (Kaya et al., pg 1123, col 1, para 1, 3).

U.S. Pat. No. 7,951,845 and issued continuation and continuation-in-part applications thereof, are directed to compositions comprising vitamin A, vitamin C, vitamin E and magnesium generally in weight ratios of approximately 1:33:12:10, and their use in treating noise-induced hearing loss, age-related hearing loss, and hearing loss caused by ototoxic antibiotics or microbes. These patents generally exemplify treating a subject with the composition before and during exposure to conditions that are associated with hearing loss, but do not exemplify or suggest a synergistic restoration of a level of hearing in a subject by administration of an improved nutraceutical suspoemulsion with enhanced oral bioavailability, nor that the formulation can synergistically restore hearing in a subject by administration at a time well after initial onset of the hearing loss.

Thus, the previous attempts at treating hearing loss have not adequately addressed the need for a stand-alone hearing loss treatment that is easy to administer, possesses enhanced bioavailability, displays minimized side effects, and provides synergistic restoration of hearing, even when treatment commences well after the initial onset of hearing loss.

SUMMARY OF THE INVENTION

There is a need for a hearing loss treatment that is easy to administer, possesses minimized side-effects that do not require adverse event monitoring by physicians and therefore does not require prescription authorization, and provides synergistic restoration of a level of hearing, even when treatment commences well after the hearing loss occurred. The present invention is directed toward further solutions to address this need, in addition to having other desirable characteristics.

In accordance with an embodiment of the present invention, a method for restoring a level of hearing in a human subject in need thereof, wherein the method comprises orally administering to the subject a nutraceutical formulation in the form of a suspoemulsion comprising: i) a magnesium compound comprising salts, salt complexes or chelates thereof; ii) Vitamin C in an amount≤5,000 IU; iii) a provitamin A carotenoid in an amount≥8,000 μg retinol activity equivalents (RAE); iv) Vitamin E; and v) a nutraceutically acceptable liquid lipophilic carrier; wherein each of i)-iv) is present in an amount, when combined together in the same formulation, to restore a level of hearing when administered to a human subject in need thereof, wherein the subject in need thereof is a subject that has already developed hearing loss, and wherein the nutraceutical formulation is encapsulated within one or more softgel capsules or twist-off softgel capsules, or is administered orally in a non-encapsulated liquid form.

In accordance with one aspect of the present invention, the nutraceutical formulation is administered once or twice daily. In accordance with one aspect of the present invention, the nutraceutical formulation is administered for a duration of at least three months.

In accordance with one aspect of the present invention, the restoration of hearing loss in the subject is determined by measuring increased distortion product otoacoustic emission (DPOAE) amplitude at one or more f2 frequencies selected from 1 kHz, 1.5 kHz, 2 kHz, 3 kHz, 4 kHz, 5 kHz, 6 kHz, 7 kHz, 8 kHz, 9 kHz or 10 kHz, when compared to measured DPOAE amplitude at these same f2 frequencies prior to initial administration of the nutraceutical formulation, and wherein the DPOAE amplitude is recorded when exposed to two pure tones f1 and f2 at a decibel sound pressure level (DB SPL) of 50-65, with a level separation of at least 10 DB SPL, and a frequency ratio of f2:f1 of approximately 1.2.

In accordance with one aspect of the present invention, the provitamin A carotenoid is a purified beta-carotene, wherein the molar ratio of the purified beta-carotene to Vitamin C is approximately 1:7 to 1:21.

In accordance with one aspect of the present invention, the provitamin A carotenoid is a purified beta-carotene, wherein the molar ratio of the purified beta-carotene to synthetic Vitamin E is approximately 1:6.5 to 1:9.5.

In accordance with one aspect of the present invention, the provitamin A carotenoid is a purified beta-carotene, wherein the molar ratio of the purified beta-carotene to the magnesium compound is approximately 1:110 to 1:120.

In accordance with one aspect of the present invention, the provitamin A carotenoid is a purified beta-carotene, the Vitamin E is a synthetic Vitamin E, and wherein the molar ratio of the purified beta-carotene, Vitamin C, the synthetic Vitamin E, and the magnesium compound is approximately 1:7-21:6.5-9.5:110-120. In accordance with one aspect of the present invention, the molar ratio of the purified beta-carotene, Vitamin C, the synthetic Vitamin E, and the magnesium compound is approximately 1:17.5:8.4:116.5.

In accordance with one aspect of the present invention, the subject in need thereof is a subject that has already developed hearing loss caused by damage to hair cells within the inner ear associated with a ciliopathy, with exposure to loud noise, or an ototoxic pharmaceutical, bacteria, virus, or other microorganism, or associated with a genetic mutation that upregulates production of reactive oxygen species within the cochlea, that disrupts ion exchange in the stria vascularis and Organ of Corti, or otherwise disturbs the formation or maintenance of the endolymphatic potential.

In accordance with an embodiment of the present invention, a method of restoring a level of hearing in a human subject in need thereof, wherein the method comprises orally administering to the subject a nutraceutical suspoemulsion consisting essentially of: i) a magnesium compound comprising salts, salt complexes or chelates thereof; ii) Vitamin C in an amount≤5,000 IU; iii) a provitamin A carotenoid in an amount≥8,000 µg retinol activity equivalents (RAE); iv) Vitamin E; and v) a nutraceutically acceptable liquid lipophilic carrier; wherein the provitamin A carotenoid is a purified beta-carotene and the Vitamin E is synthetic Vitamin E in the form of DL-alpha-Tocopheryl acetate, wherein the molar ratio of the purified beta-carotene, Vitamin C, the synthetic Vitamin E, and the magnesium compound is approximately 1:7-21:6.5-9.5:110-120, wherein the subject in need thereof is a subject that has already developed hearing loss caused by damage to hair cells within the inner ear associated with a ciliopathy, associated with exposure to loud noise, or an ototoxic pharmaceutical, bacteria, virus, or other microorganism, or associated with a genetic mutation that upregulates production of reactive oxygen species within the cochlea, that disrupts ion exchange in the stria vascularis and Organ of Corti, or otherwise disturbs the formation or maintenance of the endolymphatic potential, wherein the nutraceutical formulation is encapsulated within one or more softgel capsules or twist-off softgel capsules, or is administered orally in a non-encapsulated liquid form.

In accordance with an embodiment of the present invention, a nutraceutical formulation in the form of a suspoemulsion, for use in restoring a level of hearing in a human subject in need thereof, the nutraceutical formulation consisting essentially of: i) a magnesium compound comprising salts, salt complexes or chelates thereof; ii) Vitamin C in an amount≤5,000 IU; iii) a provitamin A carotenoid in an amount≥8,000 µg retinol activity equivalents (RAE); iv) Vitamin E; and v) a nutraceutically acceptable liquid lipophilic carrier; wherein each of i)-iv) is present in an amount, when combined together in the same formulation, to act synergistically to restore a level of hearing when administered to a human subject in need thereof, and wherein the nutraceutical formulation is encapsulated within one or more softgel capsules or twist-off softgel capsules, or is administered orally in a non-encapsulated liquid form.

In accordance with an embodiment of the present invention, a method of restoring a level of hearing in a human subject in need thereof, wherein the method comprises orally administering to the subject a nutraceutical formulation in the form of a suspoemulsion comprising: i) a magnesium compound comprising salts, salt complexes or chelates thereof; ii) Vitamin C in an amount≤5,000 IU; iii) a provitamin A carotenoid in an amount≥8,000 µg retinol activity equivalents (RAE); iv) Vitamin E; and v) a nutraceutically acceptable liquid lipophilic carrier; wherein each of i)-iv) is present in an amount, when combined together in the same formulation, to act synergistically to treat hearing loss when administered to a human subject in need thereof, wherein the subject in need thereof is a subject that has already developed hearing loss caused by damage to hair cells within the inner ear associated with a ciliopathy, with exposure to loud noise, or an ototoxic pharmaceutical, bacteria, virus, or other microorganism, or associated with a genetic mutation that upregulates production of reactive oxygen species within the cochlea, that disrupts ion exchange in the stria vascularis and Organ of Corti, or otherwise disturbs the formation or maintenance of the endolymphatic potential, and wherein the nutraceutical formulation is encapsulated within one or more softgel or twist-off softgel capsules, or is administered orally in a non-encapsulated liquid form.

In accordance with an embodiment of the present invention, a method for reducing the severity or risk of developing dementia or Alzheimer's disease, and associated cognitive decline in a human subject in need thereof, wherein the method comprises orally administering to the subject a nutraceutical formulation in the form of a suspoemulsion comprising: i) a magnesium compound comprising salts, salt complexes or chelates thereof; ii) Vitamin C in an amount≤5,000 IU; iii) a provitamin A carotenoid in an amount≥8,000 µg retinol activity equivalents (RAE); iv) Vitamin E; and v) a nutraceutically acceptable liquid lipophilic carrier; wherein each of i)-iv) is present in an amount, when combined together in the same formulation, to act synergistically to treat or reduce the likelihood of developing hearing loss when administered to a human subject in need thereof, wherein the subject in need thereof is a subject at risk of developing or has already developed hearing loss caused by damage to hair cells within the inner ear associated with a ciliopathy, with exposure to loud noise, or an ototoxic pharmaceutical, bacteria, virus, or other microorganism, or associated with a genetic mutation that upregulates production of reactive oxygen species within the cochlea, that disrupts ion exchange in the stria vascularis and Organ of Corti, or otherwise disturbs the formation or maintenance of the endolymphatic potential, or is a subject which is at risk of developing or has been diagnosed with dementia or Alzheimer's disease, and wherein the nutraceutical formulation is encapsulated within one or more softgel or twist-off softgel capsules, or is administered orally in a non-encapsulated liquid form.

In accordance with an embodiment of the present invention, a nutraceutical formulation in the form of a suspoemulsion, for use in reducing the likelihood of developing hearing loss or restoring a level of hearing in a human subject in need thereof, the nutraceutical formulation comprising: i) a magnesium compound comprising salts, salt complexes or chelates thereof; ii) Vitamin C in an amount≤5,000 IU; iii) a provitamin A carotenoid in an amount≥8,000 μg retinol activity equivalents (RAE); iv) Vitamin E; and v) a nutraceutically acceptable hydrophobic liquid carrier; wherein each of i)-iv) is present in an amount, when combined together in the same formulation, to act synergistically to reduce the likelihood of developing hearing loss or restoring a level of hearing when administered to a human subject in need thereof, and wherein the nutraceutical formulation is encapsulated within one or more softgel capsules or twist-off softgel capsules.

In accordance with aspects of the present invention, the provitamin A carotenoid is selected from the group consisting of alpha-carotene, beta-carotene, beta-cryptoxanthin, and combinations thereof. In accordance with aspects of the present invention, the provitamin A carotenoid is a purified beta-carotene. In accordance with aspects of the present invention, the molar ratio of the purified beta-carotene to Vitamin C is approximately 1:7 to 1:21.

In accordance with aspects of the present invention, the Vitamin E is a synthetic Vitamin E. In accordance with aspects of the present invention, the synthetic Vitamin E is DL-alpha-Tocopheryl acetate. In accordance with aspects of the present invention, the provitamin A carotenoid is a purified beta-carotene, and wherein the molar ratio of the purified beta-carotene to synthetic Vitamin E is approximately 1:6.5 to 1:9.5. In accordance with aspects of the present invention, the magnesium compound is selected from the group consisting of magnesium oxide, magnesium citrate, magnesium sulfate, magnesium acetate, magnesium gluconate, magnesium fumarate, magnesium chloride, magnesium glycinate, magnesium lactate, magnesium salicylate, magnesium stearate, and combinations thereof.

In accordance with aspects of the present invention, the provitamin A carotenoid is a purified beta-carotene, wherein the molar ratio of the purified beta-carotene to the magnesium compound is approximately 1:110 to 1:120.

In accordance with aspects of the present invention, the provitamin A carotenoid is a purified beta-carotene, the Vitamin E is a synthetic Vitamin E, and wherein the molar ratio of the purified beta-carotene, Vitamin C, the synthetic Vitamin E, and the magnesium compound is approximately 1:7-21:6.5-9.5:110-120. In accordance with aspects of the present invention, the molar ratio of the purified beta-carotene, Vitamin C, the synthetic Vitamin E, and the magnesium compound is approximately 1:17.5:8.4:116.5.

BRIEF DESCRIPTION OF THE FIGURES

These and other characteristics of the present invention will be more fully understood by reference to the following detailed description in conjunction with the attached drawings, in which:

FIGS. 1A/1B depict baseline graphs of DPOAE amplitude as a function of f2 frequency (DP-gram) of right and left ear respectively, indicating that Patient 1 suffers from hearing loss at all tested frequencies, prior to receiving treatment according to an embodiment of the present invention;

FIGS. 2A/2B depict DP-grams of right and left ear of Patient 1 demonstrating significant restoration of hearing at multiple frequencies after only three months of commencing treatment according to one aspect of the present invention;

FIGS. 3A/3B depict DP-grams of right and left ear of Patient 1 demonstrating significant restoration of hearing at multiple frequencies after six months of commencing treatment according to one aspect of the present invention;

FIGS. 4A/4B depict DP-grams of right and left ear of Patient 1 demonstrating significant restoration of hearing at multiple frequencies after nine months of commencing treatment according to one aspect of the present invention;

FIGS. 5A/5B depict DP-grams of right and left ear of Patient 1 demonstrating significant restoration of hearing at multiple frequencies after twelve months of commencing treatment according to one aspect of the present invention;

FIGS. 6A/6B depict DP-grams of right and left ear of Patient 1 demonstrating significant restoration of hearing at multiple frequencies after sixteen months of commencing treatment according to one aspect of the present invention;

FIGS. 7A/7B depict DP-grams of right and left ear of Patient 1 demonstrating significant restoration of hearing at multiple frequencies after twenty-four months of commencing treatment according to one aspect of the present invention;

FIGS. 8A/8B depict baseline graphs of DPOAE amplitude as a function of f2 frequency (DP-gram) of right and left ear respectively, indicating that Patient 2 suffers from hearing loss at some tested frequencies, prior to receiving treatment according to an embodiment of the present invention;

FIGS. 9A/9B depict DP-grams of right and left ear of Patient 2 demonstrating significant restoration of hearing at multiple frequencies after only three months of commencing treatment according to one aspect of the present invention;

FIGS. 10A/10B depict DP-grams of right and left ear of Patient 2 demonstrating significant restoration of hearing at multiple frequencies after six months of commencing treatment according to one aspect of the present invention;

FIGS. 12A/12B depict DP-grams of right and left ear of Patient 2 demonstrating significant restoration of hearing at multiple frequencies after twelve months of commencing treatment according to one aspect of the present invention;

FIGS. 17A/17B depict DP-grams of right and left ear of Patient 3 demonstrating significant restoration of hearing at multiple frequencies after six months of commencing treatment according to one aspect of the present invention;

FIGS. 18A/18B depict DP-grams of right and left ear of Patient 3 demonstrating significant restoration of hearing at multiple frequencies after nine months of commencing treatment according to one aspect of the present invention;

FIGS. 19A/19B depict DP-grams of right and left ear of Patient 3 demonstrating significant restoration of hearing at multiple frequencies after twelve months of commencing treatment according to one aspect of the present invention;

FIGS. 20A/20B depict DP-grams of right and left ear of Patient 3 demonstrating significant restoration of hearing at multiple frequencies after eighteen months of commencing treatment according to one aspect of the present invention.

DETAILED DESCRIPTION OF THE INVENTION

Figure 11A:
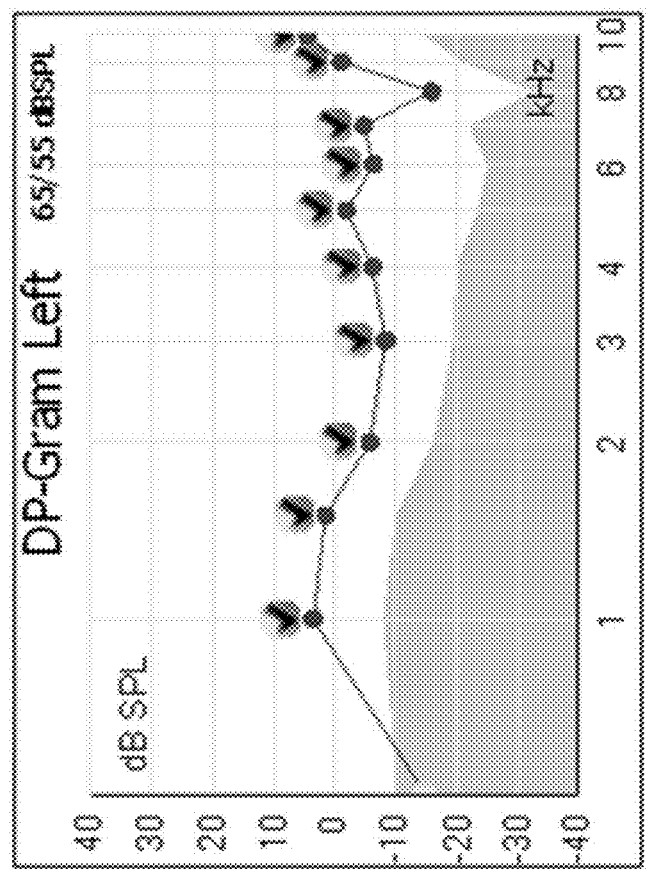
FIGS. 11A/11B depict DP-grams of right and left ear of Patient 2 demonstrating significant restoration of hearing at multiple frequencies after nine months of commencing treatment according to one aspect of the present invention.
Figure 11B:
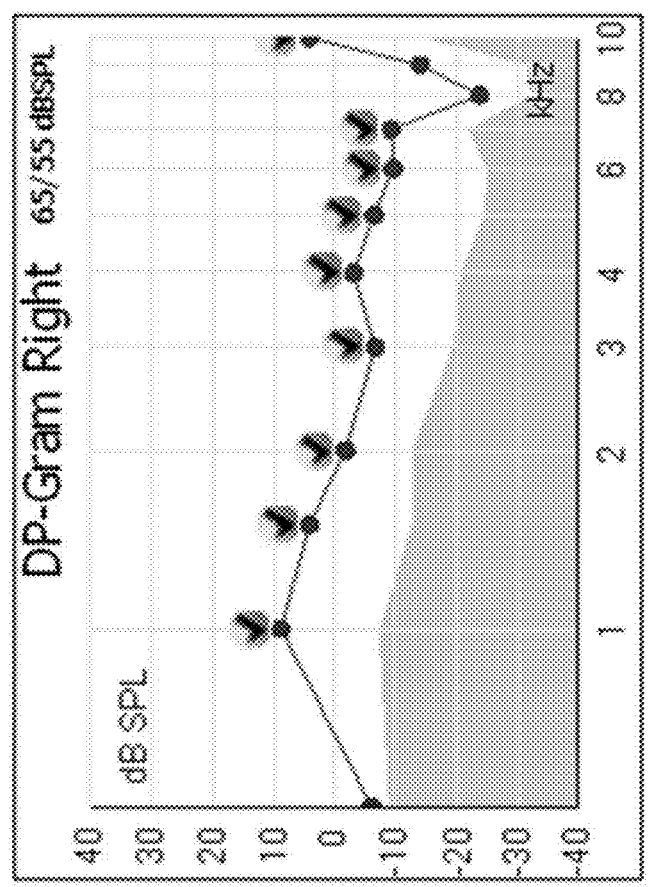
Figures 13A, 13B:
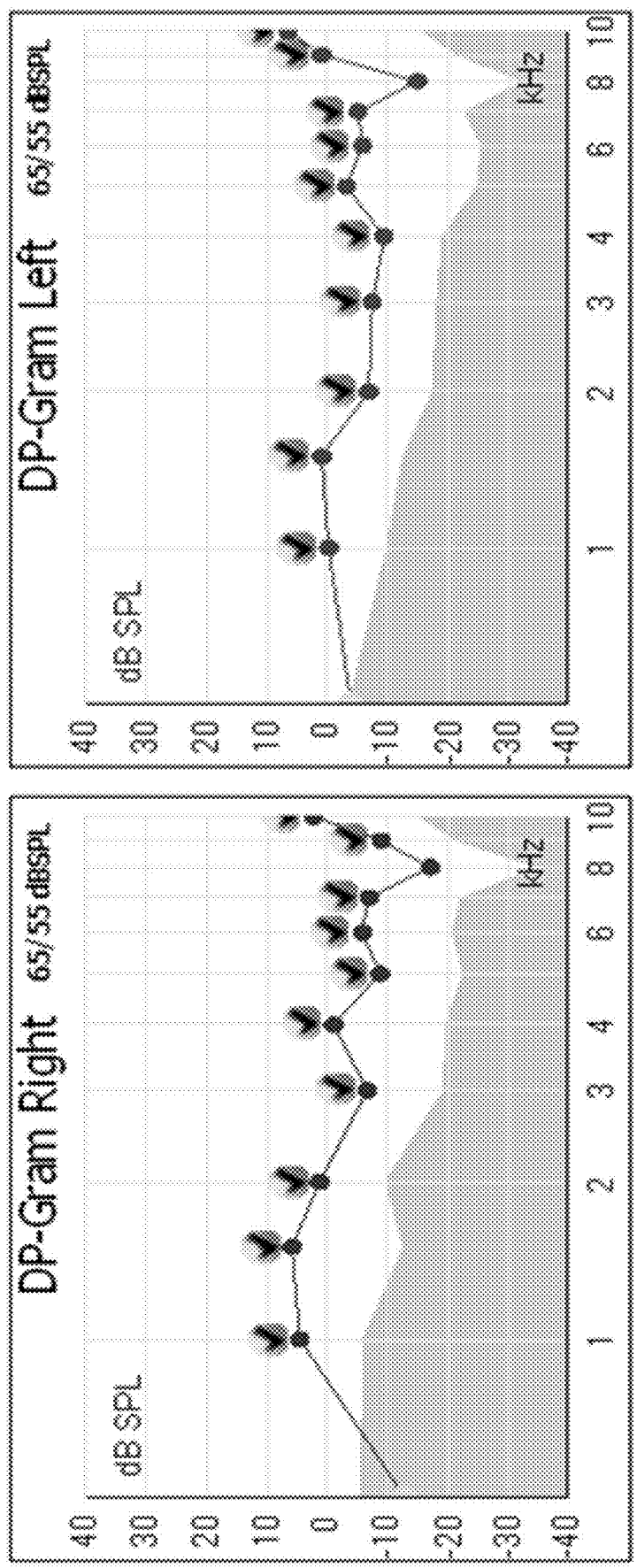
FIGS. 13A/13B depict DP-grams of right and left ear of Patient 2 demonstrating significant restoration of hearing at multiple frequencies after eighteen months of commencing treatment according to one aspect of the present invention.
Figures 14A, 14B:
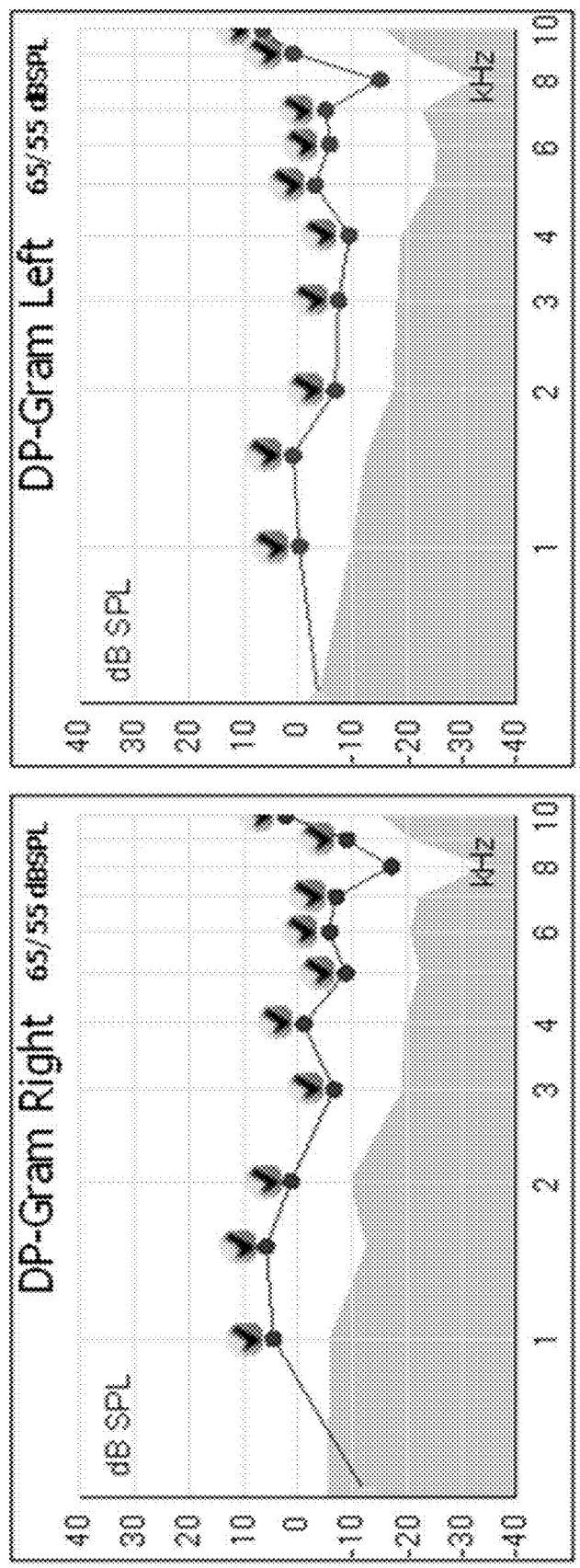
FIGS. 14A/14B depict DP-grams of right and left ear of Patient 2 demonstrating significant restoration of hearing at multiple frequencies after twenty-four months of commencing treatment according to one aspect of the present invention.

An illustrative embodiment of the present invention relates to a nutraceutical formulation and methods of their use in restoring a level of hearing in a human subject in need thereof or reducing the likelihood of developing hearing loss, the nutraceutical formulation comprising the combination of one or more of i) a magnesium compound comprising salts, salt complexes or chelates thereof; ii) Vitamin C in an amount≤5,000 IU; iii) a provitamin A carotenoid in an amount≥8,000 µg retinol activity equivalents (RAE); iv) Vitamin E; and v) a nutraceutically acceptable hydrophobic liquid carrier. In certain embodiments, the nutraceutical formulation comprises the combination of i) a magnesium compound comprising salts, salt complexes or chelates thereof; ii) Vitamin C in an amount≤ 5,000 IU; iii) a provitamin A carotenoid in an amount≥8,000 µg retinol activity equivalents (RAE); iv) Vitamin E; and v) a nutraceutically acceptable hydrophobic liquid carrier. In some embodiments, each of i)-iv) is present in an amount, when combined together in the same formulation, to act synergistically to reduce the likelihood of developing hearing loss or restoring a level of hearing when administered to a human subject in need thereof.

In some embodiments, the nutraceutical formulation described herein is used to treat hearing loss mediated by excess free radicals within the inner ear. The excess free radicals may be associated with hearing losses categorized as age-related hearing loss (ARHL), noise-induced hearing loss (NIHL), antibiotic-induced hearing loss, ciliopathy-associated hearing loss, chemotherapeutic-induced hearing loss, hearing loss caused by a bacteria, virus, or fungus or other microorganism, hearing loss associated with a genetic mutation that disrupts ion exchange in the stria vascularis and Organ of Corti, or otherwise disturbs the formation or maintenance of the endolymphatic potential, or hearing loss associated with a genetic mutation that imparts increased free radical generation in the inner ear. Additionally, the nutraceutical formulation can be used to treat trauma caused to the inner ear, by stress trauma, mechanically-induced metabolic trauma, or mechanical trauma.

In some embodiments, the nutraceutical formulation described herein is a neuroprotectant therapeutic, capable of reducing the risk of developing dementia, Alzheimer's Disease and/or cognitive decline associated therewith. In some embodiments, the nutraceutical formulation described herein is used to reduce the severity of, prevent the worsening of, or slowing the progression of developing dementia, Alzheimer Disease, and cognitive decline associated therewith. Multiple recent studies have helped to establish the link between untreated hearing loss and the development or worsening of dementia, Alzheimer's disease, and cognitive decline associated therewith. (Jiang, Fan, et al. "Association between hearing aid use and all-cause and cause-specific dementia: an analysis of the UK Biobank cohort." The Lancet Public Health 8.5 (2023): e329-e338, Livingston, Gill, et al. "Dementia prevention, intervention, and care: 2020 report of the Lancet Commission." The Lancet 396.10248 (2020): 413-446). Importantly, these studies indicate that development and worsening of dementia as well as cognitive decline associated with Alzheimer's Disease is largely prevented by treatment of hearing loss in a large number of the cohort subjects (Jiang, 2023). Thus, in certain embodiments of the invention, the nutraceutical formulation is administered to subjects at risk of age-related hearing loss in order to reduce the risk of developing dementia and/or cognitive decline associated with Alzheimer's disease. In some embodiments, the nutraceutical formulation is administered to those suffering from hearing loss to restore hearing and thus reduce the risk of developing or worsening of dementia and/or cognitive decline associated with Alzheimer's disease.

In some embodiments, the nutraceutical formulation described herein is used to treat hearing loss associated with a ciliopathy. The ciliopathy is not particularly limited and includes those disclosed herein or that are known in the literature to be associated with hearing loss. In some embodiments, the ciliopathy associated with hearing loss is associated with one or more genetic mutations which negatively impact morphology, attachment, function, or presence of the kinocilia or stereocilia of the outer or inner hair cells or which downregulate or hinder Sonic Hedgehog signaling. In some embodiments, the genetic mutation associated with ciliopathy-associated hearing loss include mutations to one or more of the genes selected from the group consisting of OSBPL2, ORP2, ORP3, ORP5, ORP8, INPP5E, LFT88, IFT25, IFT27, GMAP210, TMEM67, BBS4, BBS6, ALMS1, CEP290, TRIP11, BBS8, LFT20, TBCID32, BROMI, CILK1, PCDH15, OTX1, OTX2, ADCY6, ANKS3, ANKS6, CEP41, CNGA1, CNGA41, CNGB1, C2ORF71, C21ORF2, DCDC2, EFHC1, FLCN, GPR161, ICK, INPP5E, IQCB1, LCA5, NEK1, OCRL, PIK3R4, PKD1, PKD2, PKD1L1, RAB23, SDCCAG8, SMO, USP9X, ARL2BP, CENPF, CEP19, CEP41, CEP78, CEP104, CEP120, CSPP1, C2CD3, C21ORF2, FAM161A, FLCN, HYLS1, INTU, KIAA0556, KIZ, NEK2, NME7, OCRL, OFDI, PIBF1, PLK4, POC1B, POC1A, RAB28, RP2, TALPID3, TAPT1, TOPORS, TTLL5, TUB, WDPCP, and KIF3A. In some embodiments, the ciliopathy-associated hearing loss that may be treated with the nutraceutical formulation according to the present invention includes hearing loss in individuals that have Usher's Syndrome, Alstrom Syndrome, Joubert Syndrome, Meckel-Gruber syndrome, or Bardet-Biedl syndrome.

It has been found that many of the above insults to the ear result in the accumulation of excess free radicals within the inner ear, which in turn damage sensitive structures therein, such as inner hair cells (IHC) or outer hair cells (OHC). The damage to the sensitive structures of the ear is compounded by free radical-mediated vasoconstriction and loss of blood flow to these structures, often leading to cell death of cell populations found therein. Thus, to combat the underlying etiology of the described types of hearing loss, the nutraceutical formulation comprises a vasodilator and multiple antioxidants which act through a variety of mechanisms to synergistically mediate the effect of the presence of free radicals and resulting vasoconstriction. Without wishing to be bound by theory, it is believed that provitamin A carotenoids protect the inner ear by scavenging reactive oxygen species, such as superoxide anion radicals, singlet oxygen, hydroxyl radicals, perhydroxyl radicals and lipid peroxyl radicals, as well as reactive nitrogen species, such as nitric acid and peroxynitrite. Likewise, it is believed that the electron donor Vitamin C, protects the inner ear by scavenging reactive oxygen species and reactive nitrogen species. Vitamin E is believed to be one of the most significant antioxidants in the body, and that supplementation therewith specifically protects the cell membranes, such as mitochondrial cell membranes, within the inner ear from oxidative stress. The magnesium compound is thought to impart vasodilation to the minute vasculature within the ear, aiding the delivery of the aforementioned antioxidants, as well as other nutrients and oxygen, to the inner ear.

When all four compounds are combined in specific ratios and administered to a subject, Applicant has surprisingly found that in addition to preserving hearing or obtaining a reduction in likelihood of hearing loss in the treated subject, a synergistic restoration of a level of hearing can also be achieved. For example, the level of hearing restored to an individual experiencing hearing loss can include a restoration of 10%, 15%, 20%, 25%, 30%, 35%, 40%, 45%, 50%, 55%, 60%, 65%, 70%, 75% or more of a level of hearing. In other embodiments, hearing loss is mitigated in a subject experiencing hearing loss, such that hearing loss is reduced 10%, 15%, 20%, 25%, 30%, 35%, 40%, 45%, 50%, 55%, 60%, 65%, 70%, 75% or more in the subject. In some embodiments, a level of hearing is preserved over a period of time in a treated subject of 10%, 20%, 25%, 30%, 35%, 40%, 45%, 50%, 55%, 60%, 65%, 70%, 75%, 80%, 85%, 90%, 95% or 100% compared to a level of hearing otherwise obtained during the same period of time in the same subject without treatment with the composition. Methods used to assess this hearing restoration, reduction in hearing loss and preservation of hearing is not particularly limited and includes methods known to those of ordinary skill in the field, such as pure tone audiometry, speech discrimination tests, and so forth. In some embodiments, degree of hearing loss is assessed before initiation of treatment by measuring distortion product otoacoustic emission (DPOAE) amplitude at one or more f2 frequencies selected from 1 kHz, 1.5 kHz, 2 kHz, 3 kHz, 4 kHz, 5 kHz, 6 kHz, 7 kHz, 8 kHz, 9 kHz, or 10 kHz. The DPOAE amplitude is recorded when exposed to two pure tones f1 and f2 at a decibel sound pressure level (DB SPL) of 50-65, with a level separation of at least 10 DB SPL, and a frequency ratio of f2:f1 of approximately 1.2. Having thus established the pre-treatment hearing loss baseline DPOAE amplitudes at these one or more f2 frequencies, the level of restoration of hearing can be determined by comparing these DPOAE baseline amplitudes against measured DPOAE amplitudes at these same one or more f2 frequencies after administration of the nutraceutical formulation.

The specific ratios that result in synergistic restoration of a level of hearing, in synergistic reduction of likelihood of developing hearing loss, or reduction in severity or risk of developing or worsening of dementia, Alzheimer's, and/or cognitive decline are molar ratios based on the molar content of the provitamin A carotenoid and at least one of vitamin C, vitamin E, and magnesium salts, salt complexes, and chelates thereof. For example, in some embodiments, the provitamin A carotenoid is a purified beta-carotene. In some embodiments, the molar ratio of the provitamin A carotenoid, e.g., purified beta-carotene, to Vitamin C is approximately 1:7 to 1:25, 1:9 to 1:23, 1:11 to 1:21, or 1:12 to 1:19. In some embodiments, the molar ratio of provitamin A carotenoid to Vitamin C is approximately 1:7, 1:8, 1:9, 1:10, 1:11, 1:12, 1:13, 1:14, 1:15, 1:16, 1:17, 1:18, 1:19, 1:20, 1:21, 1:22, 1:23, 1:24, or 1:25. In one embodiment, the molar ratio of provitamin A carotenoid to vitamin C is approximately 1:17.5.

In accordance with one aspect of the present invention, the specific ratios that result in synergistic restoration of a level of hearing, in synergistic reduction of likelihood of developing hearing loss, or reduction in severity or risk of developing dementia or Alzheimer's are molar ratios based on the molar content of the provitamin A carotenoid and vitamin E. In some embodiments, the provitamin A carotenoid is a purified beta-carotene. In some embodiments, the molar ratio of the provitamin A carotenoid, e.g., purified beta-carotene, to synthetic vitamin E is approximately 1:6.5 to 1:9.5, 1:7 to 1:9, or 1:7.5 to 1:8.5. In some embodiments, the molar ratio of provitamin A carotenoid to vitamin E is approximately 1:7, 1:7.2, 1:7.4, 1:7.6, 1:7.8, 1:8, 1:8.2, 1:8.4, 1:8.6, 1:8.8, 1:9, 1:9.2, 1:9.4, 1:9.6, 1:9.8, or 1:10. In one embodiment, the molar ratio of provitamin A carotenoid to vitamin E is approximately 1:8.4.

In accordance with one aspect of the present invention, the specific ratios that result in synergistic restoration of a level of hearing, in synergistic reduction of likelihood of developing hearing loss, or reduction in severity or risk of developing dementia or Alzheimer's are molar ratios based on the molar content of the provitamin A carotenoid and the magnesium salt, salt complex or chelate thereof. In some embodiments, the provitamin A carotenoid is a purified beta-carotene. In some embodiments, the molar ratio of the provitamin A carotenoid, e.g., purified beta-carotene, to the magnesium compound is approximately 1:110 to 1:120, 1:112 to 1:119, or 1:114 to 1:118. In some embodiments, the molar ratio of provitamin A carotenoid to vitamin E is approximately 1:114, 1:114.5, 1:115, 1:115.5, 1:116, 1:116.5, 1:117, 1:117.5, 1:118, or 1:118.5. In one embodiment, the molar ratio of provitamin A carotenoid to vitamin E is approximately 1:116.5. In some embodiments, the molar ratio of provitamin A carotenoid to vitamin E is approximately 1:116. In some embodiments, the molar ratio of provitamin A carotenoid to vitamin E is approximately 1:118. In some embodiments, the molar ratio of provitamin A carotenoid to vitamin E is approximately 1:117. In some embodiments, the molar ratio of provitamin A carotenoid to vitamin E is approximately 1:115. In some embodiments, the molar ratio of provitamin A carotenoid to vitamin E is approximately 1:114.

The specific provitamin A compound that forms part of the nutraceutical formulation is not particularly limited, and includes those provitamin A compounds described herein, along with other known commercially available provitamin A compounds that do not cause toxicity when administered in daily doses higher than 8,000 mcg RAE and which are capable of scavenging reactive oxygen and/or nitrogen species. In some embodiments, the provitamin A compound comprises a compound selected from the group consisting of xanthophylls, astaxanthin, canthaxanthin, lutein, zeaxanthin, alpha-carotene, beta-carotene and beta-cryptoxanthin. In certain embodiments, the provitamin A compound is a purified beta-carotene.

The provitamin A compound is present in the composition in amounts that result in synergistic restoration of a level of hearing, or reduction in severity or risk of developing dementia or Alzheimer's in a subject to which it is administered in combination with other antioxidants and a magnesium compound. In some embodiments, the provitamin A compound is administered in an amount of at least 8,000 mcg RAE, at least 8,400 mcg RAE, at least 8,700 mcg RAE, at least 9,000 mcg, at least 11,000 mcg RAE, at least 14,000 mcg RAE, at least 18,000 mcg RAE, at least 20,000 mcg RAE, or at least 30,000 mcg RAE or more. In some embodiments, the provitamin A compound is administered in an amount of about 7,500 to 30,000 mcg RAE, 8,000 to 25,000 mcg RAE, 8,500 to 20,000 mcg RAE, or 9,000 to 18,000 mcg RAE. In some embodiments the provitamin A is administered in an amount of approximately 9,000 mcg RAE or 18,000 mcg RAE in a single dose. In some embodiments the provitamin A is administered in an amount of approximately 9,000 mcg RAE or 18,000 mcg RAE as a daily dose.

The specific vitamin C compound included in the nutraceutical formulation is not particularly limited, and includes those vitamin C compounds described herein as well as other commercially available vitamin C compounds which are capable of scavenging reactive oxygen species, reactive nitrogen species or inhibiting lipid peroxidation. In some embodiments, the vitamin C compound is selected from the group consisting of ascorbic acid, ascorbic acid salts, complexes, chelates, esters and metabolites thereof. In some embodiments, the vitamin C compound is selected from the group consisting of ascorbyl palmitate, ascorbic acid, dehydroascorbic acid, potassium ascorbate, magnesium ascorbate, zinc ascorbate, molybdenum ascorbate, chromium ascorbate, manganese ascorbate, sodium ascorbate, and calcium ascorbate or mixtures thereof. In some embodiments, the vitamin C compound comprises calcium ascorbate.

The vitamin C compound is present in the composition in amounts that result in synergistic restoration of a level of hearing, or reduction in severity or risk of developing dementia or Alzheimer's in a subject to which it is administered in combination with other antioxidants and a magnesium compound. In some embodiments, the vitamin C compound is administered in an amount of <12,000 IU, such as 3,000 IU to 10,000 IU, 3,500 IU to 8,000 IU, or 4,000 IU to 6,000 IU. When administered as part of a unit dosage form, the unit dosage form comprises the vitamin C compound in 250 mg or less. In some embodiments, the unit dosage form is administered only once per day. In some embodiments, the unit dosage form is administered twice a day.

The specific vitamin E compound included in the nutraceutical formulation is not particularly limited, and includes vitamin E compounds described herein as well as commercially available natural and synthetic vitamin E compounds, that are capable of preventing oxidation of lipid membranes. Specific mention is made of dl-alpha-tocopherol and RRR-alpha-tocopherol as well as water-soluble Tocopheryl polyethylene glycol-1000 succinate. In some embodiments, the vitamin E compound is dl-alpha-tocopherol. In some embodiments the vitamin E compound is RRR-alpha-tocopherol.

The vitamin E compound is present in the composition in amounts that result in synergistic restoration of hearing in a subject, or reduction in severity or risk of developing dementia or Alzheimer's to which it is administered in combination with other antioxidants and a magnesium compound. In some embodiments, the vitamin E compound is administered in an amount of 75-700 IU, 90-500 IU, or 100-250 IU. When administered as part of a unit dosage form, the vitamin E may be present in amounts of 100-300 mg, 100-200 mg and most preferably 125-145 mg. In some embodiments, vitamin E is present at 133.5 mg in a unit dosage form that is administered once or twice daily.

The specific magnesium compound present in the nutraceutical formulation is not particularly limited and includes those magnesium salts, complexes and chelates described herein, as well as other commercially available magnesium compounds which are capable of vasodilation when orally administered to a human subject. In some embodiments, the magnesium compounds are selected from the group consisting of magnesium oxide, magnesium citrate, magnesium sulfate, magnesium acetate, magnesium aspartate, magnesium carbonate, magnesium chloride, magnesium fumarate, magnesium gluconate, magnesium glycinate, magnesium hydroxide, magnesium lactate, magnesium salicylate, magnesium stearate, magnesium glutamate hydrobromide, magnesium hydrochloride, magnesium bisulfate, magnesium nitrate, arginate, magnesium bisglycinate, magnesium ascorbate, magnesium oxalate, magnesium valerate, magnesium oleate, magnesium palmitate, magnesium laurate, magnesium borate, magnesium benzoate, magnesium phosphate, magnesium tosylate, magnesium maleate, magnesium fumarate, magnesium succinate, magnesium taurate, magnesium tartrate, magnesium naphthenate, magnesium glucoheptonate, lauryl sulfate and mixtures thereof.

The magnesium compound is present in the composition in amounts that result in synergistic restoration of a level of hearing, or reduction in severity or risk of developing dementia or Alzheimer's to which it is administered in combination with multiple antioxidants. In particular, the magnesium is present in some embodiments in amounts of 100-500 mg, 120-400 mg, 140-300 mg, or 150-180. When present in a unit dosage form, the magnesium is present in an amount of 130-270 mg. In some embodiments, the magnesium compound is present at 157.5 mg in a unit dosage form that is administered once or twice daily.

In some embodiments, the nutraceutical formulation comprises one or more carriers and/or diluents. In some embodiments, a carrier may be a material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound within the body. Each carrier must be "acceptable" in the sense of being compatible with the other ingredients of the formulation and not injurious to the subject. Some examples of materials which can serve as carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids; (23) serum component, such as serum albumin, HDL and LDL; (24) $C_2$-$C_{12}$ alcohols, such as ethanol; and (25) other nontoxic compatible substances employed in pharmaceutical formulations. Wetting agents, coloring agents, release agents, coating agents, sweetening agents, flavoring agents, perfuming agents, preservative and antioxidants can also be present in the formulation.

In some embodiments, the nutraceutical formulation can be specially formulated for administration in solid or liquid form, including those adapted for the following: (1) oral administration, for example, suspoemulsion, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 35 3,270,960.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion. In some embodiments, the nutraceutical formulation is formulated as a suspoemulsion. In some embodiments, the nutraceutical formulation is formulated as a liquid shot, e.g., a 2 ounce liquid. When formulated as a non-encapsulated liquid, sweetening agents, fruit essences, and/or flavor oils may be included to enhance the flavor of the formulation. Additionally, when formulated as a non-encapsulated liquid, liquid diluents and thickeners may be added to facilitate case of swallowing the formulation.

For oral administration, compositions can be formulated readily by combining the active agent(s) with pharmaceutically acceptable carriers well known in the art. Such carriers enable the agents to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl cellulose, sodium carboxymethylcellulose, and/or polyvinylpyrrolidone (PVP). If desired, disintegrating agents may be added, such as the cross linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration. For buccal administration, the compositions may take the form of tablets or lozenges formulated in conventional manner.

By "treatment", "prevention" or "amelioration" of a disease or disorder is meant delaying or preventing the onset of such a disease or disorder, reversing, alleviating, ameliorating, inhibiting, slowing down or stopping the progression or severity of a condition associated with such a disease or disorder. In one embodiment, the symptoms of a disease or disorder are alleviated by at least 5%, at least 10%, at least 20%, at least 30%, at least 40%, or at least 50%.

The dosage, administration schedule and method of administering the nutraceutical formulations are not limited. The dosage may depend upon a variety of factors including other treatment, the number of doses and the individual patient parameters including age, physical condition, size and weight. These are factors well known to those of ordinary skill in the art and can be addressed with no more than routine experimentation. In some embodiments, a maximum tolerated dose may be used, that is, the highest safe and tolerable dose according to sound medical judgment. In some embodiments the dosing regimen is informed by pharmacodynamic investigations directed towards assessing the minimal and optimal doses which achieves the therapeutic effect, including restoration of hearing and reducing the risk of dementia and/or Alzheimer's Disease. In some embodiments, this approach assesses the oral dose necessary to reduce or largely eliminate free radicals within cells of the Organ of Corti, such as OHC or IHC. In some embodiments, doses sufficient to modulate mitochondrial energy production in cells within the Organ of Corti are determined. In some embodiments, where the nutraceutical formulation is to be encapsulated, the nutraceutical formulation is administered in a daily dose of 250 mg, 500 mg, 750 mg, 900 mg, 1000 mg, 1250 mg, 1500 mg, 1750 mg, 2000 mg, 2250 mg, 2500 mg, 2750 mg, 2800 mg, 2850 mg, 2900 mg, 3000 mg, 3250 mg, 3500 mg, 3750 mg, or 4000 mg. In some embodiments, the nutraceutical formulation daily dose is set based upon the weight of the patient. For example, the nutraceutical formulation may be administered in an amount of 3 mg/kg to 100 mg/kg per day. In some embodiments, the nutraceutical formulation is administered in an amount of 5 mg/kg, 6 mg/kg, 7 mg/kg, 8 mg/kg, 9 mg/kg, 10 mg/kg, 11 mg/kg, 13 mg/kg, 15 mg/kg, 17 mg/kg, 20 mg/kg, 23 mg/kg, 25 mg/kg, 28 mg/kg, 30 mg/kg, 33 mg/kg, 35 mg/kg, 38 mg/kg, 40 mg/kg, 43 mg/kg, 45 mg/kg, 48 mg/kg, 50 mg/kg, 53 mg/kg, 55 mg/kg, 58 mg/kg, 59 mg/kg, 60 mg/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 72 mg/kg, or 75 mg/kg. When the nutraceutical formulation is provided as a non-encapsulated liquid form with added diluents, the formulation may be administered in amounts up to 500 mg/kg The dose used may be the maximal tolerated dose or a sub-therapeutic dose or any dose therebetween. In some embodiments nutraceutical formulations are administered in combination with one or more agents. In particular, the nutraceutical formulation may be administered in combination with pharmaceutical agent that is known to upregulate free radicals within the inner ear. In some embodiments the nutraceutical formulation is administered with a platinum chemotherapeutic or an aminoglycoside antibiotic. In other embodiments, the nutraceutical may be administered which potentiate or enhance the action of the nutraceutical formulation. In some embodiments, the nutraceutical formulations and/or the one or more agents are administered according to a defined administration schedule. Multiple doses are contemplated. In some embodiments, when the nutraceutical formulations and one or more agents are administered in combination, a sub-therapeutic dosage of one or more of the agents may be used. A "sub-therapeutic dose" as used herein refers to a dosage which is less than that dosage which would produce a therapeutic result in the subject if administered in the absence of the other agent.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with decreased systolic heart function or ventricular arrhythmias. In addition, the methods and compositions described herein can be used to treat domesticated animals and/or pets.

The nutraceutical formulation of the invention comprises compounds that may suffer from poor bioavailability when administered orally. For example, provitamin A and vitamin E are lipophilic and have been discovered to suffer from poor uptake in the gastrointestinal tract. Furthermore, some forms of magnesium suffer from reduced water solubility and thus likewise suffer corresponding reduced uptake in the gastrointestinal tract. To enhance the bioavailability of the lipophilic compounds within the nutraceutical formulation, the nutraceutical formulation has been prepared in the form of a suspoemulsion. Orally delivered in this form, provitamin A and vitamin E demonstrate increased uptake in the gastrointestinal tract, thus potentiating the antioxidant properties of the same fixed amount of vitamin E and provitamin A. An added benefit to this approach, is that the dosage form may take a smaller profile, which increases patient compliance to the treatment regimen. Furthermore, enhancement of bio absorption of magnesium can be achieved by reducing the size of the magnesium, which aids in uptake in the gastrointestinal tract. In similar manner, the vasodilating properties of a fixed amount of magnesium can be potentiated. Thus, in some embodiments, it is desirable that the magnesium and/or the vitamin C may be provided in micronized forms.

Example 1—Restoration of Hearing in Three Patients

To further demonstrate the effectiveness of the inventive nutraceutical formulation for restoring hearing to patients suffering with hearing loss, three patients were administered two softgel capsules containing a nutraceutical formulation as presently disclosed, once daily by mouth. During the study period, a clinician conducted distortion product otoacoustic emissions (DPOAE) exams to establish a baseline level of hearing, and subsequently at three-month intervals to ascertain any improvement in hearing at the tested frequencies. The DPOAE exam is a non-invasive, objective measure of outer hair cell (OHC) function or dysfunction. OHCs are the auditory transduction cells in the Organ of Corti within the cochlea, that amplify and transform sound vibrations into electric signals, which are transferred into the auditory cortex of the brain via inner hair cells (IHCs) and the auditory nerve.

Titan DPOAE test equipment manufactured by Interacoutics, Denmark, was used DPOAE exams. The Titan equipment employs a tiny speaker and microphone inserted into the ear canal to detect OHC function autonomously, without involving actions by the test administrator or responses by the test subject, in contrast to the traditional pure tone audiometry (PTA) test that depends on both. The exam takes about four minutes for each ear, about eight minutes total, producing a binary (pass/fail) measure of OHC function at a range of low to high frequencies-1, 1.5, 2, 3, 4, 5, 6, 7, 8, 9, and 10 kHz. The DPOAE probe was calibrated daily to ensure accurate measurements. Otoscopy was performed to ensure the ear canal was clear of wax and debris. Middle ear measurements were performed to ensure the tympanic membrane and auditory ossicles (malleus, incus, and stapes) were functioning properly to transmit sound stimuli to the cochlea. DPOAE equipment calibrates and monitors ear canal noise level at −10 dB, visualized in gray. Measurements are precise, within 1-2 dB of test tones delivered at 65 and 55 dB.

Figure 15A:
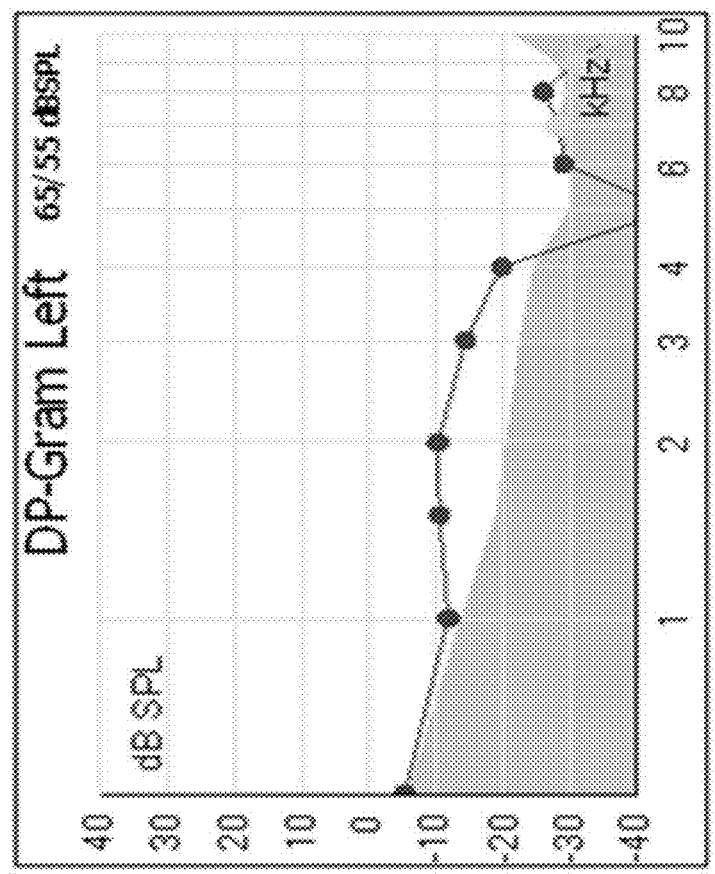
FIGS. 15A/15B depict baseline graphs of DPOAE amplitude as a function of f2 frequency (DP-gram) of right and left ear respectively, indicating that Patient 3 suffers from hearing loss at some tested frequencies, prior to receiving treatment according to an embodiment of the present invention.
Figure 15B:
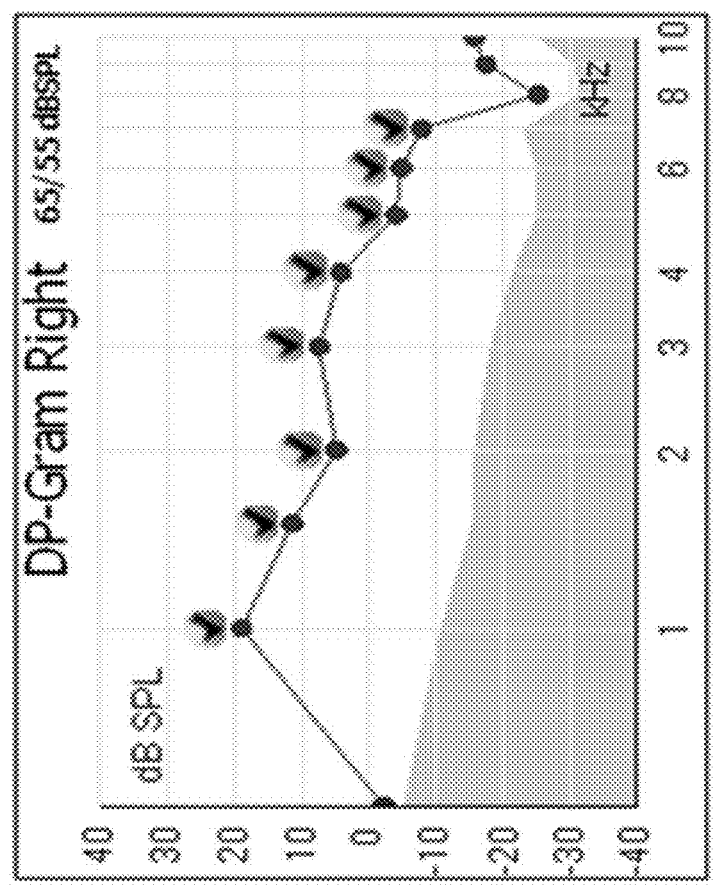
Figure 16A:
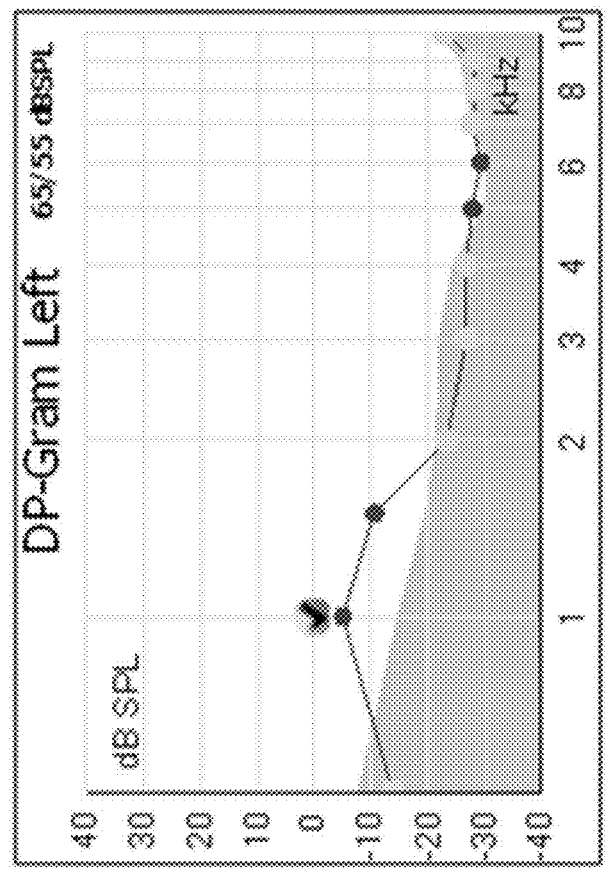
FIGS. 16A/16B depict DP-grams of right and left ear of Patient 3 demonstrating significant restoration of hearing at multiple frequencies after only three months of commencing treatment according to one aspect of the present invention.
Figure 16B:
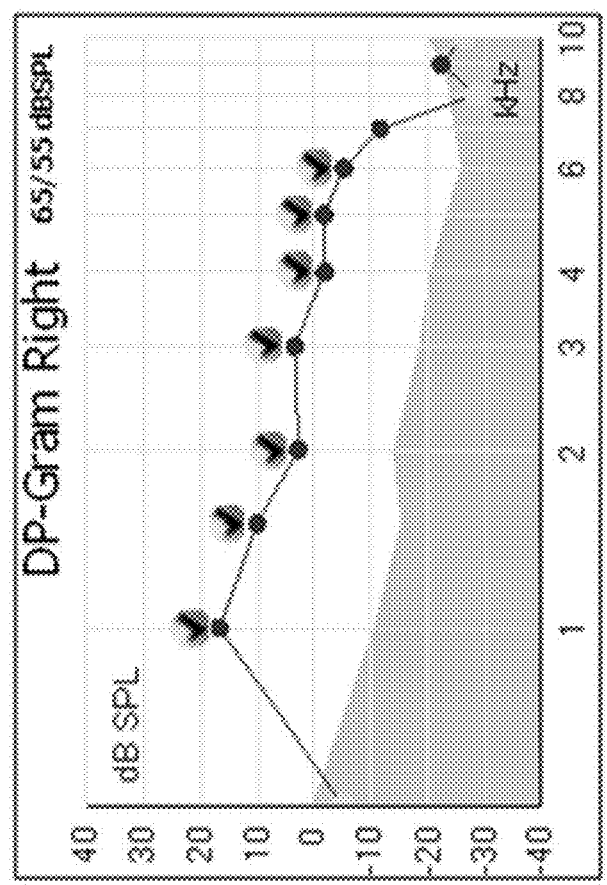
Figure 21A:
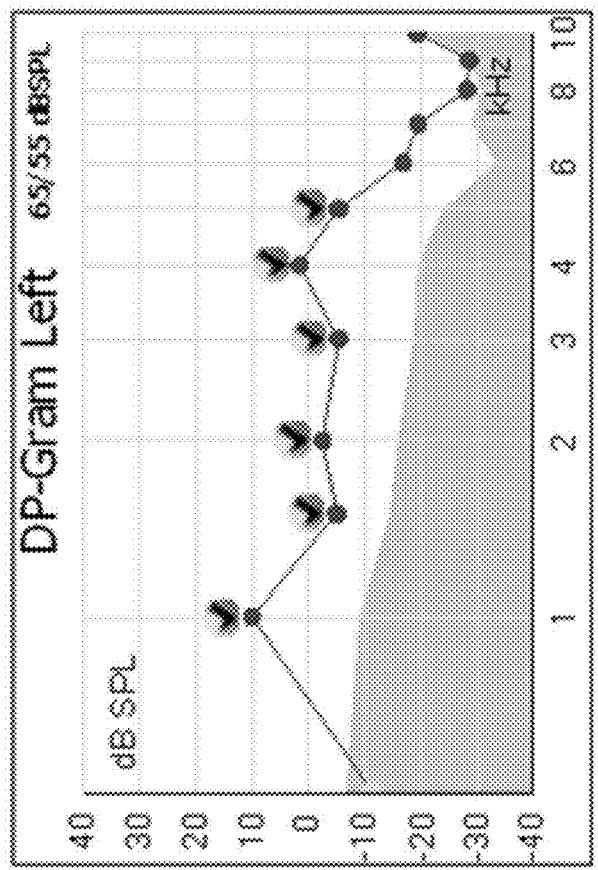
FIGS. 21A/21B depict DP-grams of right and left ear of Patient 3 demonstrating significant restoration of hearing at multiple frequencies after twenty-four months of commencing treatment according to one aspect of the present invention.
Figure 21B:
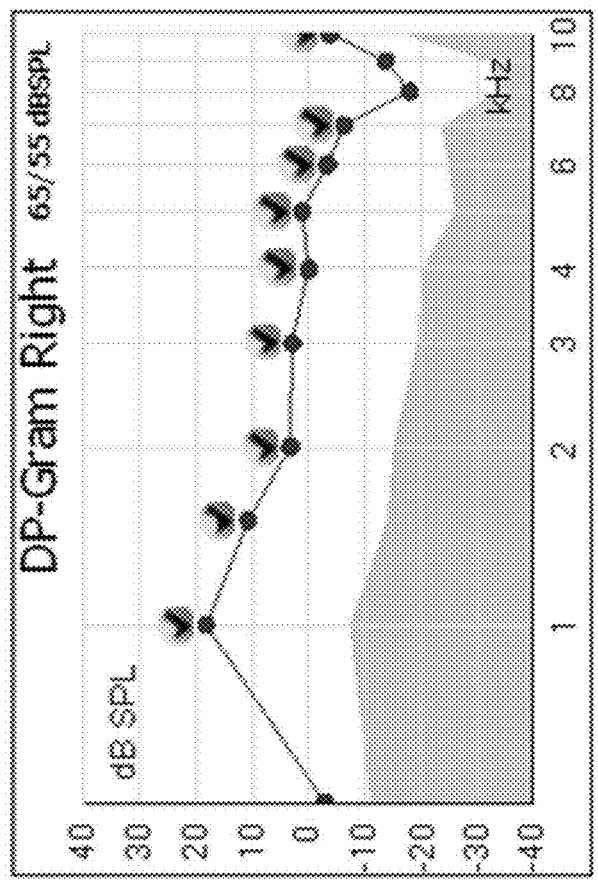

Turning to the figures, a checkmark within a circle depicted in the DP grams provided in all of FIGS. 1A to 21B inclusive, indicates that OHCs in the frequency range under test have reached the 'pass' threshold. OHCs that fail to be detected (thus no checkmark) indicate clinically significant OHC damage and dysfunction greater than 40 to 50 dB, generally considered as permanent, nonrecoverable hearing impairment in the frequency range under test. As can be seen in FIGS. 1A and 1B, which represent the result of DPOAE exams on the right and left ears of Patient 1, respectively, Patient 1 exhibits clinically significant hearing impairment in the frequency ranges under test. Similarly, Patient 2 showed clinically significant hearing impairment at 8 kHz and 9 kHz in the right ear (FIG. 8A), and at 4 kHz-10 kHz in the left ear (FIG. 8B). A baseline examination of Patient 3 also revealed clinically significant hearing impairment at 8 kHz-10 kHz in the right ear (FIG. 15A) and all frequencies tested in the left ear (FIG. 15B).

Despite conventional medical wisdom indicating that impairment of OHC auditory function is not reversible, the quarterly DPOAE exam data for each patient demonstrates OHC auditory function and resulting hearing can be restored in patients receiving the nutraceutical formulation, as disclosed herein. For example, FIGS. 2A and 2B, demonstrate that clinically significant hearing could be restored in Patient 1, even within 3 months of treatment with the inventive composition, demonstrated by 9 passing scores in the tested frequencies within the right and left ears, where there were 0 passing scores at baseline. Following this trend, both patients 2 and 3 also demonstrate restoration of hearing after 3 months on the disclosed treatment, as shown by the greater total number of passing scores obtained on the 3 month DPOAE tests compared to baseline tests in each individual (FIGS. 9A, 9B, 16A, 16B).

With the exception of patient 1, with lapsed treatments between periods 2 and 3 as well as between periods 5 and 6, regular administration of the disclosed composition to all three patients resulted in durable restoration of hearing, which showed a trend towards increasing OHC auditory function and auditory sensitivity over time, as seen in test results of all three patients (see e.g. FIGS. 3A, 3B, 4A, 4B, 6A, 6B, 10A, 10B, 11A, 11B, 12A, 12B, 13A, 13B, 14A, 14B, 17A, 17B, 18A, 18B, 19A, 19B, 20A, 20B, 21A, 21B). Furthermore, while Patient 1 experienced a regression in OHC auditory function after lapse of treatment, resumption of treatment resulted in recovery of the lost auditory function (see FIGS. 5A, 5B, 7A, 7B). Thus, it is clear that administration of the disclosed composition to those suffering hearing loss results in significant restoration of OHC auditory function and hearing among the frequencies tested.

Example 2—Real-World Evidence Study

Overview

The worldwide hearing loss disability for more than 1.5 billion disproportionately affects the lives and livelihoods of those in low- and middle-income countries (LMIC) [1]. Hearing aids are the predominant treatment; however, their impact is modest, and they are less available in LMIC where the need is greatest [2, 3]. Moreover, hearing loss is the #1 mid-life risk factor for dementia [4].

Sensorineural hearing loss (SNHL), the most common form of hearing loss [5], is a metabolic stress disorder compounded by vasospasm, leading to mitochondrial DNA (mtDNA) dysfunction [6, 7].

The micronutrient formula ACEMg was developed to block SNHL and successfully tested on animal models [8]. Findings were reported from a real-world evidence (RWE) study (N=190) conducted to assess whether ACEMg impacts SNHL in humans.

Real-world data (RWD) from distortion product otoacoustic emissions (DPOAE) examinations were collected from patients previously diagnosed with SNHL. DPOAE examinations produce objective measures of the auditory function of outer hair cells (OHC) in the cochlea [9].

Analyses of RWD from DPOAE examinations in the treatment group (N=93), who used ACEMg as softgel capsules, compared with DPOAE RWD from the untreated group (N=97) demonstrate ACEMg significantly stabilized and improved auditory function. DPOAE scores over two years increased or remained unchanged for 75.3% in the treatment group. DPOAE scores decreased by 73.2% for those in the untreated group (X21, 190=44.61, p<0.001).

The findings justify additional RWE studies to quantify ACEMg impact further.

Introduction

The World Health Organization (W.H.O.) describes hearing loss as a major global health issue, an unmet health and medical need that decreases the quality of life at any age, estimating current annual economic costs to be nearly one trillion dollars. Hearing loss is associated with social isolation, cognitive impairments, educational challenges, underemployment, and higher rates of unemployment [Ibid. 1]. Moreover, hearing loss in midlife is the number one risk factor for dementia (Alzheimer's disease) [Ibid. 4]. By 2050, approximately 10% of the world population, or 2.5 billion people, are projected to have a degree of hearing loss [10].

The hearing loss problem is most acute in the younger population. The W.H.O. estimates "Over 1 billion people aged 12 to 35 years risk losing their hearing due to prolonged and excessive exposure to loud music and other recreational sounds. This can have devastating consequences for their physical and mental health, education, and employment prospects."

SNHL is the most common form of hearing loss [Ibid. 5], arising from a variety of etiologies including age (presbycusis), ototoxic pharmaceuticals, certain genetic mutations, viral or bacterial infection, but principally from noise exposure [Ibid. 5].

Measurably reducing the economic and social burdens associated with SNHL was the overarching motivation for the basic research on SNHL beginning in the late 1980s at the Kresge Hearing Research Institute at the University of Michigan Medical School under the direction of its director, Josef M. Miller, Ph.D., supported by grants from the National Institute on Deafness and Other Communication Disorders (NIDCD) at the National Institutes of Health (NIH).

Basic research in free radical biology demonstrated their role in inducing pathology from a wide variety of etiological factors, acting as triggers that upregulate apoptotic pathways to cell damage and dysfunction in a variety of contexts, including visible light [12, 13]; solar and ionizing radiation [14, 15]; cigarette smoke [16, 17]; hyper- and hypoxia [18, 19, 20]; pharmaceuticals [21, 22]; and intense noise exposure [23, Ibid. 3]. Cell death initiated or enhanced by free radicals continues to be studied across a broad range of pathologies in the peripheral and central nervous systems [24].

This evidence on the key role of free radicals in cell dysfunction provided theoretical and empirical support for the hypothesis that it plays a role in hearing impairment. Indeed, evidence for the efficacy of antioxidant treatment to prevent free radical-induced pathology in the eye [25] and ear [26], supported the idea that antioxidant interventions might be beneficial in preventing or ameliorating SNHL.

Thus, SNHL can be described as a metabolic stress disorder caused by excess inner ear free radicals, reactive oxygen species (ROS) formed as byproducts of mitochondrial metabolism. The resulting oxidative stress disrupts normal biochemical processes, damages mitochondria and other organelles, upregulates genes involved in cell death pathways, leading to auditory path dysfunction experienced as hearing loss [27, 28].

The high-potency ACEMg formulation of antioxidants Vitamins A, C, and E and the vasodilator Magnesium developed in the Miller laboratory was demonstrated to protect against noise induced hearing loss [Ibid. 8]. These findings, and additional Phase I, II and III translational studies under FDA IND [29], funded by the NIDCD [30, 31] and a BfArM (Germany) IMPD study funded by a European Commission medical innovation grant [32, 33, 34] resulted in nine U.S. patents for ACEMg issued to the University of Michigan as a method of treating of SNHL from noise, aging, certain ototoxic pharmaceuticals, genetic mutations and viruses, and tinnitus [35].

The ACEMg formulation was licensed to a public benefit corporation that produced an updated and improved softgel capsule oral dose format of the ACEMg formula. ACEMg is regulated as a dietary supplement under FDA DSHEA law, available to the general public without a prescription because ACEMg consists of vitamins and minerals known to be safe for humans, classified as Generally Regarded as Safe (GRAS) by the FDA [36]. Under the Soundbites trademark, ACEMg softgel capsules for adults have been in limited direct distribution since late 2019. ACEMg twist-off softgel capsules for children have been in limited direct distribution since mid 2023.

The inherent safety of ACEMg and its availability as softgel capsules enabled an initial Phase IV post-marketing real-world evidence clinical study to assess whether ongoing, daily oral self-administration of ACEMg would inhibit further hearing loss in those who had been previously diagnosed with SNHL.

Method

This is a retrospective analysis of real-world data (RWD) from audiology patients previously assessed with progressive SNHL. Because the research assesses the impact of a dietary supplement on the structure or function of the human body, it is exempt from IND requirements [37]. Regardless, the dataset was fully de-identified in accordance with 45 CFR 164.502 (d), and 164.514 (a)-(c) and also meets IRB exempt research requirements under 46 CFR 104 (d4ii).

Hearing Measures

The most common hearing test is the pure tone audiometry (PTA) examination in which tones at varying frequencies and intensities are played through headphones, and the individual indicates whether they can hear the tone. As such, the PTA examination requires a subjective response.

For clinical research purposes, however, an objective technique for testing hearing is required. The DPOAE examination assesses inner ear auditory function by recording responses generated by mechano-electrical transduction of OHC in the Organ of Corti within the cochlea. A tiny probe containing a microphone and a speaker is inserted into the ear canal, which is sealed with an earplug. Paired tones at various frequencies are emitted by the speaker. In response, OHC function at or above the lower detectable limit emits an acoustic wave (an otoacoustic emission) which can be detected by the microphone and measured by the DPOAE system. If OHC do not respond at a given frequency at a lower limit of sensitivity, hearing at that frequency is classified as not functioning [38]. This has been considered a final determination, as there is significant scientific agreement that OHC function that cannot be detected by DPOAE examination indicates total hearing impairment at the tested frequency. Thus, DPOAE is an objective measurement of cochlear function not subject to expectation or attention effects [39].

DPOAE measurements were made by a licensed, trained professional in private clinical examination rooms using an Interacoustics Titan DPOAE system. Measurements were performed in both ears at ten different frequencies (1000, 1500, 2000, 3000, 4000, 5000, 6000, 7000, 8000, 9000, and 10000 Hz). The measurements are binary: either a detectable otoacoustic emission is emitted at each of the frequencies (indicating OHC function at that frequency) or it is not. With 10 otoacoustic measures for each ear, a total of 20 binary measurements were available for analysis. An individual with hearing within normal parameters would have detectable otoacoustic emissions at all frequencies in both ears; as SNHL progresses, the percentage of frequencies at which otoacoustic emissions are detectable decreases. Therefore, in this study analyses were conducted on the percentage of the potential total of 20 frequencies present in each exam, with a range of 0% (no detectable cochlear function in either ear at any frequency) to 100% (cochlear function within normal parameters in both cars at all frequencies).

All statistical analyses were conducted using the JASP 18.2 implementation of R.

Study Sample

Two groups of patients who had been diagnosed with SNHL (N=190) were compared: the ACEMg treatment group and the no-treatment group. As a real-world evidence study of existing patient records, subjects were not randomly assigned to condition.

The ACEMg treatment group (N=93) consisted of all SNHL patients whose records included an annual DPOAE test for a total of five years: three years before starting ACEMg and two years after. In addition to the annual DPOAE examination, subjects in the ACEMg treatment group had DPOAE testing at 3, 6, and 9 months after beginning ACEMg. The study agent was ACEMg softgel capsules, available under the Soundbites trademark. Patients self-administered two softgel capsules daily by mouth at a time of their convenience.

The no-treatment group consisted of all individuals diagnosed with SNHL who had annual DPOAE test data for five consecutive years; these were individuals for whom this data was available from the years before ACEMg softgel capsules were available. The purpose of the no-treatment group is to provide a baseline of the typical rate of change in auditory function for those with SNHL over five years.

To serve as an appropriate comparison, it is important that the degree of SNHL in the two groups-ACEMg and no-treatment—in the three years before the administration of ACEMg are similar. First, the mean DPOAE scores of the two groups are not significantly different (F1,188=. 50, n.s.). Second, both groups show a reduction in DPOAE scores over the first three years (F2,376=36.81, p<0.001) with a mean DPOAE score of 39.81% in the first year and 32.21% in the third year; this is consistent with other longitudinal research which indicates that hearing loss appears to be continuous and gradual [40, 41]. Finally, and importantly, there is no difference in the amount of reduction in DPOAE scores for the two groups as indicated by the lack of an interaction between Group and Year (F2,376=1.01, n.s.).

While a smaller proportion of the females received ACEMg, this difference is not significant (43.40% females and 55.95%; X21,190-2.96, n.s.). There is a statistically significant difference in average age (62.0 in the ACEMg group and 75.3 in the no-treatment group; (F1,188=28.52, p<0.001). With a range of ages of 19 to 88 in the ACEMg group and 22 to 100 in the no-treatment group, the distribution of ages is statistically equal as indicated by the equality of variances (Levine's test F1, 188=1.62, n.s.). As a result, age is used as a covariate in the primary analyses.

Statistical Analysis of ACEMg Effects

Figure 22:
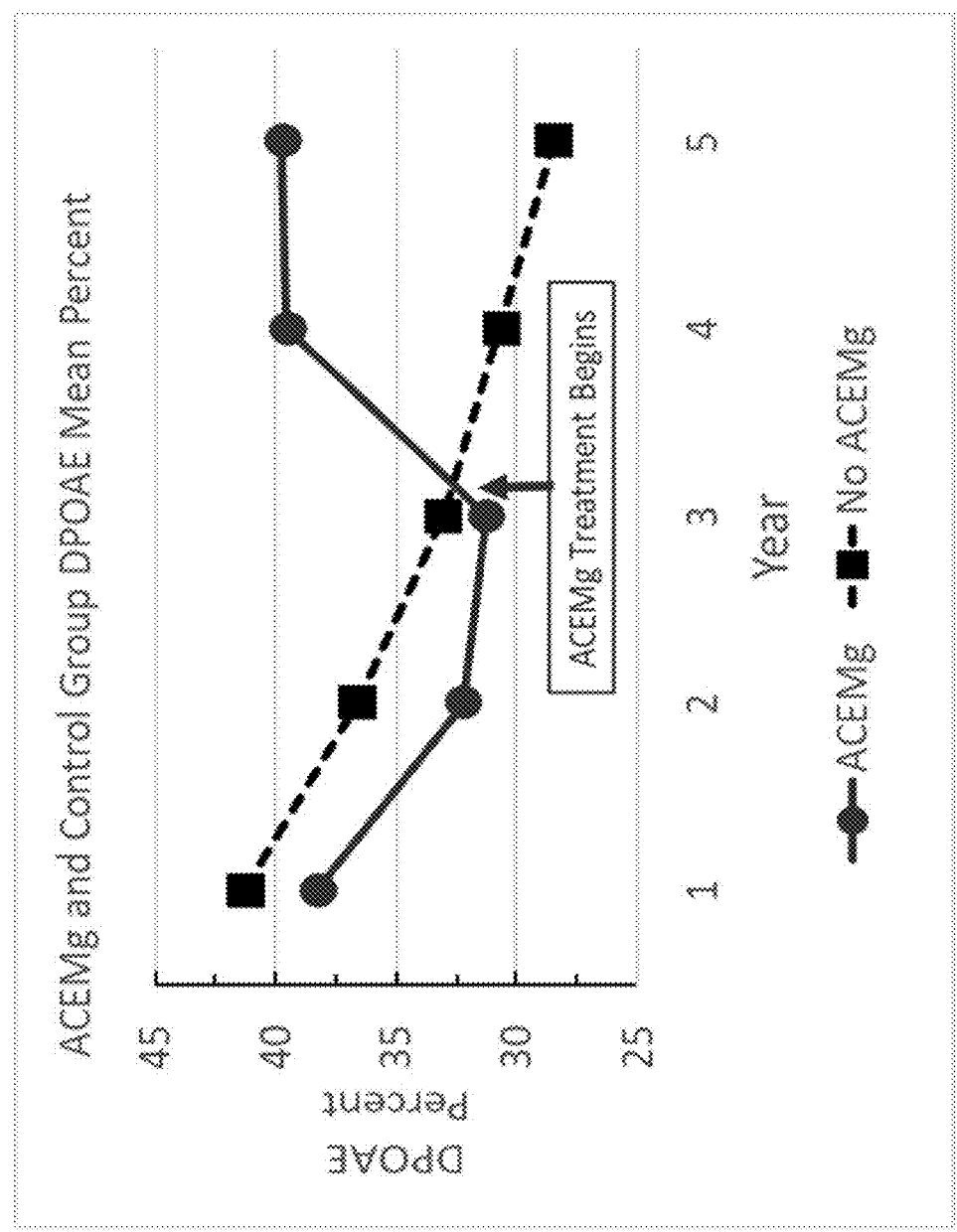
FIG. 22 depicts a comparison of the change in hearing over five years as measured by DPOAE scores for those in the ACEMg study with those in the non-treatment group.

The primary analysis of the effect of ACEMg is a comparison of the change in hearing over five years as measured by DPOAE scores for those in the ACEMg with those in the no-treatment group. FIG. 22 presents this comparison.

This pattern of DPOAE scores may be statistically analyzed by a mixed-design ANOVA of Group (ACEMg vs. no-treatment) and Year (five years of DPOAE measures for each subject), with Age as a covariate as shown in Table 1.

TABLE 1

Effects of ACEMg Group over Five Years

| Source | Sum of Squares | df | Mean Square | F | Significance |
|---|---|---|---|---|---|
| Year | 945.67 | 3.15 | 300.24 | 2.35 | n.s. |
| Year by Group | 10115.52 | 3.15 | 3211.54 | 25.13 | <.0001 |
| Year by Age | 676.31 | 3.15 | 214.72 | 1.68 | n.s. |
| Residual | 75259.48 | 589.00 | 127.77 | | |
| Group | 20377.18 | 1 | 20377.18 | 7.12 | <.01 |
| Age | 229822.01 | 1 | 229882.01 | 80.31 | <.0001 |
| Residual | 535285.42 | 187 | 2862.49 | | | note:
fractional df are based on conservative Greenhouse-Geisser adjustments due to a violation of sphericity Year and Group are the first significant effects to consider. However, the significant interaction of Year with Group makes interpreting these effects not meaningful. That is, whether hearing on average changes over five years or the ACEMg group on average hears better is not relevant. Whether hearing changes in the years of the study after one group begins taking ACEMg is important. This effect is tested statistically by the interaction of Year by Group, which is highly significant, and apparent in the pattern of results in FIG. 22.

A Tukey HSD test provides pairwise comparisons of means, with significance adjusted for the number of cases. With five pairwise comparisons (Year 1 ACEMg vs. no-treatment, Year 2 ACEMg vs. no-treatment, etc.), a difference in means of 5.21 is required for significance at the $p<0.01$ level. This difference is exceeded only in Year 4 (mean difference of 8.85) and Year 5 (mean difference of 11.25). These differences are significant at the $p<0.001$ level, which requires a mean difference of 7.03. Thus, ACEMg has a statistically positive effect on hearing.

Figure 23:
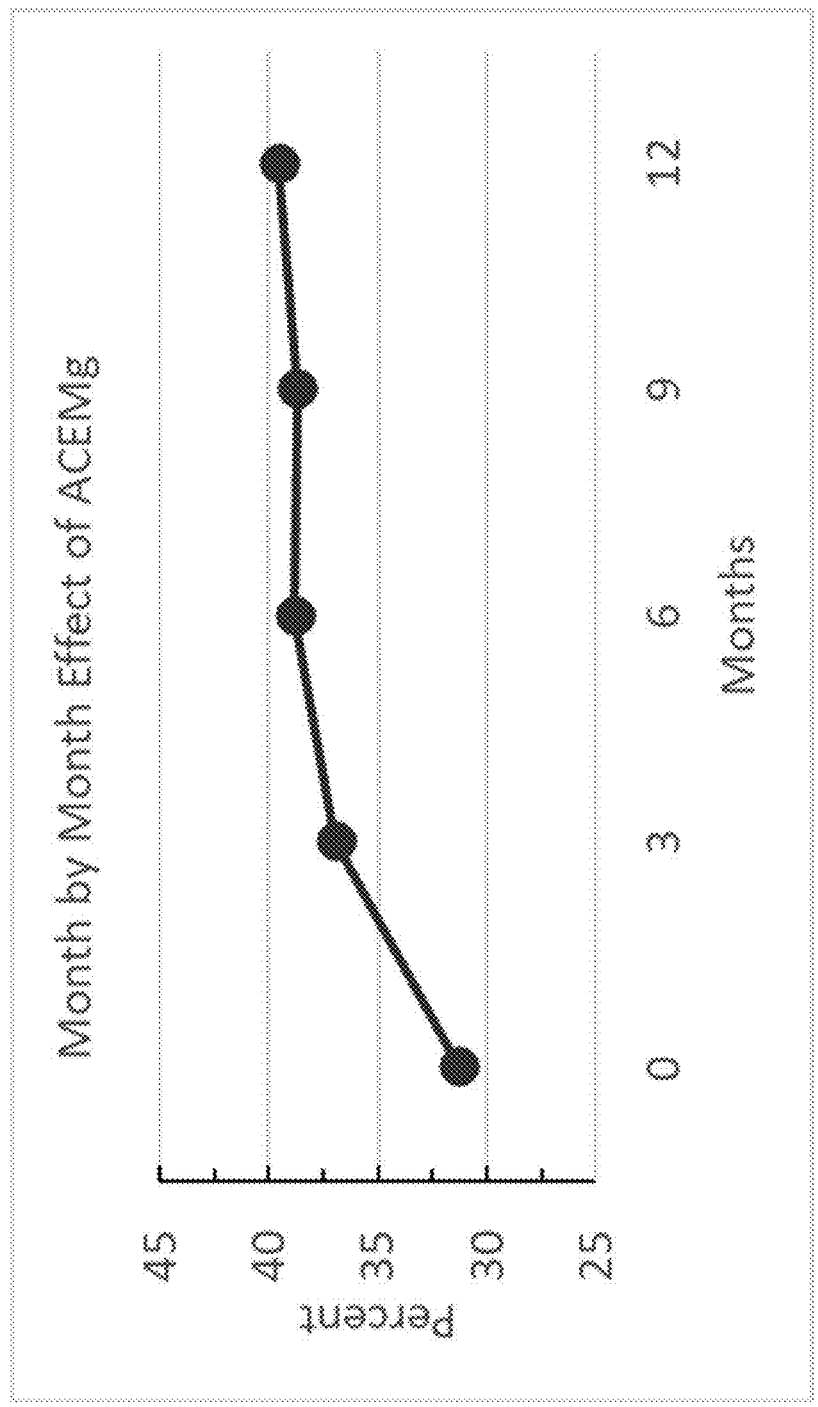
FIG. 23 depicts the time it takes for ACEMg to have an impact on hearing.

As stated above, those in the ACEMg group had their hearing tested every three months after starting to take ACEMg in addition to the annual testing. The time it takes for ACEMg to have an impact may be seen in FIG. 23. The effect of ACEMg is apparent within six months.

There is also a significant effect for Age on DPOAE scores; this is to be expected since subjects varied in age from 19 to 100. The fact that the Year-by-Age interaction is not significant indicates that the age of subjects did not affect the impact of ACEMg.

Finally, it is instructive to note that, as shown in Table 2, DPOAE scores in the ACEMg group, recorded over five years, either increased or remained unchanged for 75.3%. In contrast, over the same time frame, 73.2% of the no-treatment group recorded decreased DPOAE scores (X21, 190=44.61, $p<0.001$).

TABLE 2

Percent of Subjects with DPOAE Change Year 1 to Year 5

| Group | Decrease | Improve or No Change |
|---|---|---|
| ACEMg | 24.7% | 75.3% |
| Control | 73.2% | 28.8% |

Discussion

Pharmaceuticals to treat SNHL are unavailable today. Hearing regeneration pharmaceuticals are years away, and general availability is unlikely as is access to cochlear implant devices [43]. Earplugs, earmuffs, noise-canceling headphones and earbuds mitigate noise exposure, but they are only modestly effective, and unlikely to be continuously worn. Hearing aids help but are unaffordable for LMIC populations. "For all [LMIC] regions that make up 85% of the world population, the [hearing aid] coverage ranges from 1.5% to 12%" [44].

This study tested the potential of the safe ACEMg formula to impact hearing preservation, relying on objective auditory function data from annual DPOAE examinations among audiology patients previously diagnosed with SNHL. The no-treatment group (N=97) represented the current standard of care for SNHL. Analysis of real-world, no-treatment data validated the common understanding that hearing loss progresses over time.

DPOAE annual examination data from the two most recent years was available for those in the ACEMg treatment group (N=93). This group started taking ACEMg immediately after the third-year DPOAE examination.

Annual DPOAE examination data among adults with SNHL is unusual. Conventional wisdom is that hearing loss is permanent; therefore, repeated DPOAE examinations are considered unwarranted if a DPOAE examination cannot detect OHC function, especially in speech range frequencies. The study hypothesized that ACEMg would be shown to preserve auditory function if DPOAE scores in the ACEMg treatment group declined less than DPOAE scores in the no-treatment group.

Study findings exceeded expectations. DPOAE scores in the ACEMg group markedly improved within six months of taking ACEMg daily, demonstrating that ACEMg mitigated SNHL and improved auditory function. It is believed that these clinical findings are unprecedented in the field of therapeutic interventions for hearing preservation.

Given the vast global dimensions of the hearing loss problem and the absence of effective preventive care interventions, ACEMg might potentially contribute to hearing health preventive medicine and public health by helping reduce existing and forecast SNHL burdens.

The journey to this destination started in 1954 when the free radical theory of cell aging was proposed as a major risk factor for disease, cell dysfunction, and the aging process. In theory, excess reactive oxygen species (ROS), byproducts of metabolism in cell mitochondria not removed by antioxidant defenses, could be expected to damage cell function [45].

ACEMg applies the free radical theory to inner ear pathology. Studies started by demonstrating glutathione in endogenous cochlear cell antioxidant systems modulate noise-induced pathology [46]. Further studies demonstrated noise exposure upregulated endogenous antioxidant systems [47]; aging increases sensitivity to SNHL [48]; neurotrophins have antioxidant properties demonstrated to reduce noise-induced SNHL [49]; a variety of agents that prevent free radical-induced lipid peroxidation also prevent noise-induced SNHL [50]; Calcineurin activation contributes to the noise-induced SNHL pathway [51]; dexamethasone steroid could attenuate noise-induced SNHL [52]; antioxidant treatment following noise exposure could prevent noise-induced SNHL [53]; ischemia-reperfusion injury, or vasospasm, is involved [54]; and finally, gene expression of proteins initiate pathways to cell damage [55].

SNHL pathogenesis is a consequence of increased demand for cochlear energy production, generating a vast influx of cochlear ROS that overwhelms the endogenous antioxidant system. Residual superoxides and singlet oxygen ROS interfere with redox reactions, causing lipid peroxidation that weakens membranes, alters cell proteins, and hastens cell aging. ROS penetrate the outer mitochondrial membrane, interfering with the function of other organelles. Finally, vasospasm induces mtDNA expression of abnormal proteins leading to cell dysfunction or cell death at worst, experienced as hearing loss [56].

A consensus has emerged from ongoing research to treat SNHL with mitochondrial-targeted antioxidants [57], as SNHL pathogenesis and pathophysiology are consistent with pathologies in other organs and the brain, peripheral and central nervous system disorders, aging disorders, and environmental stress [58].

Each component in the ACEMg formula contributes a necessary mechanism of action resulting in a prophylactic composition that blocks the initiating events triggering SNHL. β-carotene (provitamin A) scavenges singlet oxygen. Singlet oxygen reacts with lipids to form lipid hydroperoxides; removing singlet oxygen prevents lipid peroxidation [59]. Donor antioxidant vitamin E removes free radicals from the lipid compartments, also reacting with and reducing peroxyl radicals, inhibiting the spread of lipid peroxidation. Vitamin C detoxifies by scavenging oxygen radicals in the aqueous phase and blocks lipid peroxidation by free radicals that "escape" neutralization by vitamins A and E [60, 61, 62]. Supplemental magnesium reduces vasoconstriction and reperfusion injury, which attenuates SNHL [Ibid. 8].

In laboratory research, ACEMg demonstrated an unexpected beneficial synergistic effect, measurably reducing NIHL at 4, 8, and 16 kHz far better than treatment with antioxidants A, C, and E together, or treatment with magnesium Mg alone, or saline, the control. ACEMg increased the noise tolerance of cochlear cells by an average of 31 dB over the control, maintaining normal auditory function when sound pressure level increased by as much as 10 times, reducing hearing loss from noise by 75% [Ibid 8].

CONCLUSION

This study yielded statistically reliable real-world clinical data demonstrating objectively measurable hearing preservation impacts of ACEMg, effectively preserving and improving auditory function, thereby mitigating SNHL.

SNHL is a metabolic stress disorder, not a disease, and ACEMg is a safe oral biomedicine, not a pharmaceutical. It was concluded that additional ACEMg RWE studies are justified, especially considering the inherent safety of ACEMg and its availability in an inexpensive, convenient oral dose form. Such studies can further assess the potential for ACEMg to impact SNHL from noise, and investigate its impact on a wider range of SNHL etiologies including side effects of ototoxic drugs and certain genetic mutations [64, 65], perhaps leading to consideration of ACEMg as an effective, accessible method of addressing the global challenge of hearing loss.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is also to be understood that the following claims are to cover all generic and specific features of the invention described herein, and all statements of the scope of the invention which, as a matter of language, might be said to fall therebetween.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

As used herein "A and/or B", where A and B are different claim terms, generally means at least one of A, B, or both A and B. For example, one sequence which is complementary to and/or hybridizes to another sequence includes (i) one sequence which is complementary to the other sequence even though the one sequence may not necessarily hybridize to the other sequence under all conditions, (ii) one sequence which hybridizes to the other sequence even if the one sequence is not perfectly complementary to the other sequence, and (iii) sequences which are both complementary to and hybridize to the other sequence.

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

REFERENCES

1. The Lancet Global Burden of Disease Study, Oct. 17, 2020 Volume 396, Global burden of 87 risk factors in 204 countries and territories; a systematic analysis for the Global Burden of Disease Study 2019, The Lancet, 396 (2020) 1223-1249. doi:10.1016/S0140-6736(20)30752-2.
2. Schuh, Marissa R, and Matthew L Bush. "Evaluating Equity Through the Social Determinants of Hearing Health." Ear and hearing vol. 43, Suppl 1 (2022): 15S-22S. doi:10.1097/AUD.0000000000001188
3. Chadha S, Kamenov K, Cieza A. The world report on hearing, 2021. Bull World Health Organ. 2021 Apr. 1; 99(4):242-242A. doi: 10.2471/BLT.21.285643. PMID: 33953438; PMCID: PMC8085630.
4. Livingston G, Huntley J, Sommerlad A, Ames D, Ballard C, Banerjee S, Brayne C, Burns A, Cohen-Mansfield J, Cooper C, Costafreda S G, Dias A, Fox N, Gitlin L N, Howard R, Kales H C, Kivimäki M, Larson E B, Ogunniyi A, Orgeta V, Ritchie K, Rockwood K, Sampson E L, Samus Q, Schneider L S, Selbæk G, Teri L, Mukadam N. Dementia prevention, intervention, and care: 2020 report of the Lancet Commission. Lancet. 2020 Aug. 8; 396 (10248):413-446. doi: 10.1016/S0140-6736(20)30367-6. Epub 2020 Jul. 30. Erratum in: Lancet. 2023 Sep. 30; 402(10408):1132. PMID: 32738937; PMCID: PMC7392084.
5. Tanna R J, Lin J W, De Jesus O. Sensorineural Hearing Loss. [Updated 2023 Aug. 23]. In: StatPearls [Internet]. Treasure Island (FL): StatPearls Publishing; 2023 January. Available from: ncbi.nlm.nih.gov/books/NBK565860/6.
6. Eisenhut M. Evidence Supporting the Hypothesis That Inflammation-Induced Vasospasm Is Involved in the Pathogenesis of Acquired Sensorineural Hearing Loss. Int J Otolaryngol. 2019; 2019:4367240. Published 2019 Nov. 6. doi:10.1155/2019/4367240

7. Alvarado, Juan C et al. "Oral Antioxidant Vitamins and Magnesium Limit Noise-Induced Hearing Loss by Promoting Sensory Hair Cell Survival: Role of Antioxidant Enzymes and Apoptosis Genes." Antioxidants (Basel, Switzerland) vol. 9, 12 1177. 25 Nov. 2020, doi:10.3390/antiox9121177

8. Le Prell C G, Hughes L F, Miller J M. Free radical scavengers vitamins A, C, and E plus magnesium reduce noise trauma. Free Radic Biol Med. 2007 May 1; 42(9):1454-63. doi: 10.1016/j.freeradbiomed.2007.02.008. Epub 2007 Feb. 20. PMID: 17395018; PMCID: PMC1950331

9. Zelle, D et al. "Objective audiometry with DPOAEs: New findings for generation mechanisms and clinical applications." "Objektive Hördiagnostik mit DPOAE: Neue Erkenntnisse zur Generierung und klinischen Anwendung." *HNO* vol. 65,Suppl 2 (2017): 122-129. doi:10.1007/s00106-016-0267-y 10. Chadha S, Kamenov K, Cieza A. The world report on hearing, 2021. Bull World Health Organ. 2021 Apr. 1; 99(4):242-242A. doi: 10.2471/BLT.21.285643. PMID: 33953438; PMCID: PMC8085630.

11. Dillard L K, Arunda M O, Lopez-Perez L, Martinez R X, Jiménez L, Chadha S. Prevalence and global estimates of unsafe listening practices in adolescents and young adults: a systematic review and meta-analysis. BMJ Glob Health. 2022 November; 7(11):e010501. doi: 10.1136/bmjgh-2022-010501. PMID: 36379592; PMCID: PMC9723884.

12. Agarwal, M. L., Larkin, H. E., Zaidi, S. I., Mukhtar, H., and Oleinick, N. L. (1993) Phospholipase Activation Triggers Apoptosis in Photosensitized Mouse Lymphoma Cells. Cancer Res 53:5897-5902.

13. Oleinick, N. L., and Evans, H. H. (1998). The Photobiology of Photodynamic Therapy: Cellular Targets and Mechanisms. Radiat. Res. 150: S146-S156.

14. Godar, D. E., and Lucas, A. D. (1995). Spectral Dependence of UV-induced Immediate and Delayed Apoptosis: The Role of membrane and DNA Damage. Photochem. Photobiol. 62:108-113.

15. Godar, D. E. (1999). Light and Death: Photons and Apoptosis. J. Investig. Dermatol. Symp. Proc 4:17-23.

16. Aoshiba, K., Tamaoki, J., and Nagai, A. (2001). Acute Cigarette Smoke Exposure Induces Apoptosis of Alveolar Macrophages. Am. J. Physiol. 281:L1392-L1401.

17. Carnevali, S., Petruzzelli, S., Longoni, B., Vanacore, R., Barale, R., Cipollini, M., Scatena, F., Paggiaro, P., Celi, A., and Giuntini, C. (2003) Cigarette Smoke Extract Induces Oxidative Stress and Apoptosis in Human Lung Fibroblasts. Am J. Physiol. 284: L955-L963.

18. Budinger, G. R., Tso, M., McClintock, D. S., Dean, D. A., Sznajder, J. I., and Chandel, N. S. (2002). Hyperoxia-induced Apoptosis Does Not Require Mitochondrial Reactive Oxygen Species and is Regulated by Bcl-2 Proteins. J. Biol. Chem. 277:15654-15660.

19. Wang, X., Ryter, S. W., Dai, C., Tang, Z. L., Watkins, S. C., Yin, X. M., Song, R., and Choi, A. M. (2003). Necrotic Cell Death in Response to Oxidant Stress Involves the Activation of the Apoptogenic Caspase-8/bid Pathway. J. Biol. Chem. 278:29184-29191.

20. Wang, X., Zhang, J., Kim, H. P., Wang, Y., Choi, A. M., and Ryter, S. W. (2004). Bcl-XL Disrupts Death-Inducing Signal Complex Formation in Plasma Membrane Induced by Hypoxia/Reoxygenation. FASEB J. 18:1826-1833.

21. Forge, A., and Schacht, J., (2000) Aminoglycoside Antibiotics. Audiol. Neurootol. 5:3-22. Godar, D. E. (1999). Light and Death: Photons and Apoptosis. J. Investig. Dermatol. Symp. Proc 4:17-23.

22. Rybak, L. P., and Ramkumar, V. (2007). Ototoxicity. Kidney International 72:931-935. Ryter, S. W., Kim, H. P., Hoetzel, A., Park, J. W., Nakahira, K., Wang, X., and Choi, A. M. K. (2007).

23. Ohinata, Y., Miller, J. M., Schacht, J. (2003). Protection from noise-induced lipid peroxidation and hair cell loss in the cochlea. Brain Research 966:2:265-273.

24. Jomova K, Raptova R, Alomar S Y, Alwasel S H, Nepovimova E, Kuca K, Valko M. Reactive oxygen species, toxicity, oxidative stress, and antioxidants: chronic diseases and aging. Arch Toxicol. 2023 October; 97(10):2499-2574. doi: 10.1007/s00204-023-03562-9. Epub 2023 Aug. 19. PMID: 37597078; PMCID: PMC10475008.

25. Age-Related Eye Disease Study Research Group. A randomized, placebo-controlled, clinical trial of high-dose supplementation with vitamins C and E and beta carotene for age-related cataract and vision loss: AREDS report no. 9. Arch Ophthalmol. 2001 October; 119(10):1439-52. doi: 10.1001/archopht.119.10.1439. Erratum in: Arch Ophthalmol. 2008 September; 126(9):1251. PMID: 11594943; PMCID: PMC1472812.

26. Sha, S. H., Qiu, J. H., Schacht, J. (2006). Aspirin Attenuates Gentamicin-Induced Hearing Loss. New Engl. J. Med 354:1856-1857.

27. Op de Beeck K, Schacht J, Van Camp G. Apoptosis in acquired and genetic hearing impairment: the programmed death of the hair cell. *Hear Res.* 2011; 281(1-2):18-27. doi: 10.1016/j.heares.2011.07.002

28. O'Sullivan J D B, Bullen A, Mann Z F. Mitochondrial form and function in hair cells. Hear Res. 2023 February; 428:108660. doi: 10.1016/j.heares.2022.108660. Epub 2022 Nov. 25. PMID: 36525891; PMCID: PMC10227193.

29. FDA IND #108,497, confidential under 21 CFR § 20.61; 5 USC 552 (b)(4), submitted by the University of Michigan Health System, Jul. 18, 2012.

30. Le Prell C G, Johnson A C, Lindblad A C, et al. Increased vitamin plasma levels in Swedish military personnel treated with nutrients prior to automatic weapon training. *Noise Health.* 2011; 13(55):432-443. doi: 10.4103/1463-1741.90317

31. Le Prell C G, Hensley B N, Campbell K C, Hall J W 3rd, Guire K. Evidence of hearing loss in a 'normally-hearing' college-student population. *Int J Audiol.* 2011; 50 Suppl 1 (Suppl 1): S21-S31. doi: 10.3109/14992027.2010.540722

32. Scheper, Verena et al. "Randomized placebo-controlled clinical trial investigating the effect of antioxidants and a vasodilator on overall safety and residual hearing preservation in cochlear implant patients." *Trials* vol. 21,1 643. 14 Jul. 2020, doi: 10.1186/s13063-020-04522-9

33. "A novel micronutrient-based strategy to prevent hearing impairments: test and road to market for age-related hearing loss and preservation of residual hearing", https://cordis.europa.eu/project/id/304925

34. Final Report Summary—PROHEARING Consortium, available from cordis.europa.eu/project/id/304925/reporting/it 35. U.S. Pat. No. 7,951,845: Composition and method of treating noise-induced hearing loss (NIHL); U.S. Pat. No. 8,338,397: Composition and method of treating side effects from aminoglycoside antibiotic treatment; U.S. Pat. No. 8,338,398: Composition for treating noise-induced hearing loss (NIHL); U.S. Pat. No. 8,927,528: Composition for treating noise-induced hearing loss (NIHL); U.S. Pat. No. 9,144,565: Method for treating hearing loss from the GJB2 connexin 26 genetic mutation; U.S. Pat. No. 9,889,156: Method for treating noise-induced hearing loss (NIHL); U.S. Pat. No. 9,770,433: Method for treating tinnitus and hearing loss; U.S. Pat. No. 9,919,008: Method for treating age-related hearing loss (ARHL); U.S. Pat. No. 10,238,599: Composition and method for treating congenital cytomegalovirus induced hearing loss.
36. FDA guidance available from fda.gov/food/food-ingredients-packaging/generally-recognized-safe-gras
37. FDA guidance available from fda.gov/about-fda/center-drug-evaluation-and-research-cder/frequently-asked-questions-botanical-drug-product-development
38. Vaden K I, Neely S T, Harris S E, Dubno J R. Metabolic and Sensory Components of Age-Related Hearing Loss: Associations With Distortion- and Reflection-Based Otoacoustic Emissions. Trends in Hearing. 2023; 27. doi: 10.1177/23312165231213776
39. Vaden K I, Neely S T, Harris S E, Dubno J R. Metabolic and Sensory Components of Age-Related Hearing Loss: Associations With Distortion- and Reflection-Based Otoacoustic Emissions. Trends in Hearing. 2023; 27. doi:10.1177/23312165231213776
40. Davis A C, Ostri B, Parving A. Longitudinal study of hearing. Acta Otolaryngol Suppl. 1990; 476:12-22. doi: 10.3109/00016489109127251. PMID: 2087950.
41. Humes L E. Longitudinal Changes in Auditory and Cognitive Function in Middle-Aged and Older Adults. J Speech Lang Hear Res. 2021 Jan. 14; 64(1):230-249. doi: 10.1044/2020_JSLHR-20-00274. Epub 2021 Jan. 5. PMID: 33400551; PMCID: PMC8608226.
42. Lye, Joey et al. "Recent Therapeutic Progress and Future Perspectives for the Treatment of Hearing Loss." *Biomedicines* vol. 11,12 3347. 18 Dec. 2023, doi:10.3390/biomedicines11123347
43. Schuh M, Bush M L. Defining Disparities in Cochlear Implantation through the Social Determinants of Health. Semin Hear. 2021 Dec. 9; 42(4):321-330. doi: 10.1055/s-0041-1739282. PMID: 34912160; PMCID: PMC8660167.
44. Nikolai Bisgaard, Stefan Zimmer, Mark Laureyns & Jennifer Groth (2022) A model for estimating hearing aid coverage world-wide using historical data on hearing aid sales, International Journal of Audiology, 61:10, 841-849, DOI: 10.1080/14992027.2021.1962551
45. Harman D. Free radical theory of aging: history. EXS. 1992; 62:1-10. doi: 10.1007/978-3-0348-7460-1_1
46. Yamasoba T, Nuttall A L, Harris C, Raphael Y, Miller J M. Role of glutathione in protection against noise-induced hearing loss. Brain Res. 1998 Feb. 16; 784(1-2): 82-90. doi: 10.1016/s0006-8993(97)01156-6. PMID: 9518561.
47. Yamasoba, Tatsuya; Harris, Craig; Shoji, Fumi; Lee, Rosanna J.; Nuttall, Alfred L.; Miller, Josef M. (August 1998). "Influence of intense sound exposure on glutathione synthesis in the cochlea". *Brain Research*. 804 (1): 72-78.
48. Shoji, F.; Miller, A. L.; Mitchell, A.; Yamasoba, T.; Altschuler, R. A.; Miller, J. M. (August 2000). "Differential protective effects of neurotrophins in the attenuation of noise-induced hair cell loss". *Hearing Research*. 146 (1-2): 134-142.
49. Shoji, Fumi; Yamasoba, Tatsuya; Magal, Ella; Dolan, David F.; Altschuler, Richard A.; Miller, Josef M. (April 2000). "Glial cell line-derived neurotrophic factor has a dose dependent influence on noise-induced hearing loss in the guinea pig cochlea". *Hearing Research*. 142 (1-2): 41-55.
50. Ohinata, Yoshimitsu; Miller, Josef M.; Schacht, Jochen (2003-03-21). "Protection from noise-induced lipid peroxidation and hair cell loss in the cochlea". *Brain Research*. 966 (2): 265-273. PMID 12618349.
51. Minami, Shujiro B.; Yamashita, Daisuke; Schacht, Jochen; Miller, Josef M. (2004-11-01). "Calcineurin activation contributes to noise-induced hearing loss". *Journal of Neuroscience Research*. 78 (3): 383-392. PMID 15389832.
52. Takemura, Keiji; Komeda, Mototane; Yagi, Masao; Himeno, Chiemi; Izumikawa, Masahiko; Doi, Tadashi; Kuriyama, Hiromichi; Miller, Josef M.; Yamashita, Toshio (2004). "Direct inner ear infusion of dexamethasone attenuates noise-induced trauma in guinea pig". *Hearing Research*. 196 (1-2): 58-68. PMID 15464302
53. Yamashita, Daisuke; Jiang, Hong-Yan; Schacht, Jochen; Miller, Josef M. (2004-09-03). "Delayed production of free radicals following noise exposure". *Brain Research*. 1019 (1-2): 201-209. PMID 15306254.
54. Eisenhut M. Evidence Supporting the Hypothesis That Inflammation-Induced Vasospasm Is Involved in the Pathogenesis of Acquired Sensorineural Hearing Loss. *Int J Otolaryngol*. 2019; 2019:4367240. Published 2019 Nov. 6. doi:10.1155/2019/4367240
55. Yamashita, Daisuke; Miller, Josef M.; Jiang, Hong-Yan; Minami, Shujiro B.; Schacht, Jochen (2004-12-22). "AIF and EndoG in noise-induced hearing loss". *Neuroreport*. 15 (18): 2719-2722. PMID 15597041.
56. Alvarado, Juan C et al. "Oral Antioxidant Vitamins and Magnesium Limit Noise-Induced Hearing Loss by Promoting Sensory Hair Cell Survival: Role of Antioxidant Enzymes and Apoptosis Genes." *Antioxidants (Basel, Switzerland)* vol. 9,12 1177. 25 Nov. 2020, doi:10.3390/antiox9121177
57. Fujimoto, Chisato; Yamasoba, Tatsuya (2019-04-24). "Mitochondria-Targeted Antioxidants for Treatment of Hearing Loss: A Systematic Review". *Antioxidants (Basel, Switzerland)*. 8 (4). PMID 31022870.
58. Lobo, V et al. "Free radicals, antioxidants and functional foods: Impact on human health." *Pharmacognosy reviews* vol. 4,8 (2010): 118-26. doi:10.4103/0973-7847.70902
59. Schafer, Freya Q.; Wang, Hong P.; Kelley, Eric E.; Cueno, Kate L.; Martin, Sean M.; Buettner, Garry R. (2002). "Comparing beta-carotene, vitamin E and nitric oxide as membrane antioxidants". *Biological Chemistry*. 383 (3-4): 671-681. ISSN 1431-6730, PMID 12033456.
60. Niki, E. (1987). "Interaction of ascorbate and alpha-tocopherol". *Annals of the New York Academy of Sciences*. 498:186-199. ISSN 0077-8923, PMID 3304060.
61. Niki, E. (1987). "Lipid antioxidants: how they may act in biological systems". *The British Journal of Cancer. Supplement*. 8:153-157. ISSN 0306-9443, PMC 2149475, PMID 3307868.
62. Evans, P.; Halliwell, B. (1999-11-28). "Free radicals and hearing. Cause, consequence, and criteria". *Annals of the New York Academy of Sciences*. 884:19-40. ISSN 0077-8923. PMID 10842581.
63. Forge, A., and Schacht, J., (2000) Aminoglycoside Antibiotics. Audiol. Neurootol. 5:3-22. Godar, D. E. (1999). Light and Death: Photons and Apoptosis. J. Investig. Dermatol. Symp. Proc 4:17-23.
64. Thatcher, Aaron; Le Prell, Colleen; Miller, Josef; Green, Glenn (2014). "ACEMg supplementation ameliorates progressive Connexin 26 hearing loss in a child". *International Journal of Pediatric Otorhinolaryngology.* 78 (3): 563-565. PMID 24439969.

65. Green, Kari L.; Swiderski, Donald L.; Prieskorn, Diane M.; DeRemer, Susan J.; Beyer. Lisa A.; Miller. Josef M.; Green, Glenn E.; Raphacl, Ychoash (2016-03-11). "ACEMg Dict Supplement Modifies Progression of Hereditary Deafness". *Scientific Reports.* 6 (1): 1-12.

What is claimed is:

1. A method for restoring a level of hearing in a human subject in need thereof, wherein the method comprises orally administering to the subject a nutraceutical formulation in the form of a suspoemulsion comprising:
   i) a magnesium compound comprising salts, salt complexes or chelates thereof;
   ii) Vitamin C in an amount≤5,000 IU;
   iii) a provitamin A carotenoid in an amount ≥8,000 ug retinol activity equivalents (RAE);
   iv) Vitamin E; and
   v) a nutraceutically acceptable liquid lipophilic carrier;
   wherein each of i)-iv) is present in an amount, when combined together in the same formulation, to synergistically restore a level of hearing when administered to a human subject in need thereof, wherein the molar ratio of the provitamin A carotenoid, the Vitamin C, the Vitamin E, and the magnesium compound is approximately 1:7-21:6.5-9.5:110-120, and
   wherein the subject has already developed hearing loss, wherein the hearing loss is not caused by a viral infection.

2. The method of claim 1, wherein the nutraceutical formulation is encapsulated within one or more twist-off softgel capsules.

3. The method of claim 1, wherein the nutraceutical formulation is encapsulated within one or more softgel capsules.

4. The method of claim 1, wherein the nutraceutical formulation is administered orally in a non-encapsulated liquid form.

5. The method of claim 1, wherein the nutraceutical formulation is administered once or twice daily.

6. The method of claim 1, wherein the provitamin A carotenoid is a purified beta-carotene.

7. The method of claim 6, wherein the Vitamin E is a synthetic Vitamin E.

8. The method of claim 5, wherein the nutraceutical formulation is administered for a duration of at least three months.

9. The method of claim 1, wherein the nutraceutical formulation is administered to a patient in an amount of 3 to 100 mg per kilogram of the patient's weight per day.

10. The method of claim 7, wherein the molar ratio of the purified beta-carotene, Vitamin C, the synthetic Vitamin E, and the magnesium compound is approximately 1:17.5:8.4:116.5.

11. The method of claim 1, wherein the subject in need thereof is a subject that has already developed hearing loss caused by damage to hair cells within the inner ear associated with a ciliopathy, with age-related hearing loss, with exposure to loud noise, or an ototoxic pharmaceutical, or bacteria, or associated with a genetic mutation that upregulates production of reactive oxygen species within the cochlea, that disrupts ion exchange in the stria vascularis and Organ of Corti, or otherwise disturbs the formation or maintenance of the endolymphatic potential.

12. A method for restoring a level of hearing in a human subject in need thereof, wherein the method comprises orally administering to the subject a nutraceutical formulation consisting essentially of:
   i) a magnesium compound comprising salts, salt complexes or chelates thereof;
   ii) Vitamin C in an amount≤5,000 IU;
   iii) a provitamin A carotenoid in an amount ≥8,000 µg retinol activity equivalents (RAE);
   iv) Vitamin E; and
   v) a nutraceutically acceptable liquid lipophilic carrier;
   wherein the provitamin A carotenoid is a purified beta-carotene and the Vitamin E is synthetic Vitamin E in the form of DL-alpha-Tocopheryl acetate,
   wherein the molar ratio of the purified beta-carotene, Vitamin C, the synthetic Vitamin E, and the magnesium compound is approximately 1:7-21:6.5-9.5:110-120, and
   wherein the subject in need thereof is a subject that has already developed hearing loss caused by damage to hair cells within the inner ear associated with a ciliopathy, with age-related hearing loss, with exposure to loud noise, or an ototoxic pharmaceutical, or bacteria, or associated with a genetic mutation that upregulates production of reactive oxygen species within the cochlea, that disrupts ion exchange in the stria vascularis and Organ of Corti, or otherwise disturbs the formation or maintenance of the endolymphatic potential,
   wherein the nutraceutical formulation is encapsulated in one or more softgel capsules or twist-off softgel capsules, or administered orally in a non-encapsulated liquid form, and
   wherein the hearing loss is not caused by a viral infection.

13. A method for reducing the severity or risk of developing dementia or Alzheimer's disease, and associated cognitive decline in a human subject in need thereof, wherein the method comprises orally administering to the subject a nutraceutical formulation consisting essentially of:
   i) a magnesium compound comprising salts, salt complexes or chelates thereof;
   ii) Vitamin C in an amount≤5,000 IU;
   iii) a provitamin A carotenoid in an amount ≥8,000 µg retinol activity equivalents (RAE);
   iv) Vitamin E; and
   v) a nutraceutically acceptable liquid lipophilic carrier;
   wherein the provitamin A carotenoid is a purified beta-carotene and the Vitamin E is synthetic Vitamin E in the form of DL-alpha-Tocopheryl acetate,
   wherein the molar ratio of the purified beta-carotene, Vitamin C, the synthetic Vitamin E, and the magnesium compound is approximately 1:7-21:6.5-9.5:110-120, and
   wherein the subject in need thereof is a subject that is at risk of developing, or has already developed hearing loss caused by damage to hair cells within the inner ear associated with a ciliopathy, with age-related hearing loss, with exposure to loud noise, or an ototoxic pharmaceutical, bacteria, or associated with a genetic mutation that upregulates production of reactive oxygen species within the cochlea, that disrupts ion exchange in the stria vascularis and Organ of Corti, or otherwise disturbs the formation or maintenance of the endolymphatic potential, or is a subject that is at risk of developing or has been diagnosed with dementia or Alzheimer's disease, wherein the hearing loss is not caused by a viral infection, and wherein the nutraceutical formulation is encapsulated in one or more softgel capsules or twist-off softgel capsules, or is administered orally in a non-encapsulated liquid form.

14. The method of claim 13, wherein the nutraceutical formulation is administered once or twice daily.

15. A method of restoring a level of hearing or reducing hearing loss in a human subject in need thereof, wherein the method comprises orally administering to the subject a nutraceutical formulation in the form of a suspoemulsion comprising:
   i) a magnesium compound comprising salts, salt complexes or chelates thereof;
   ii) Vitamin C in an amount≤5,000 IU;
   iii) a provitamin A carotenoid in an amount ≥8,000 μg retinol activity equivalents (RAE);
   iv) Vitamin E; and
   v) a nutraceutically acceptable liquid lipophilic carrier;
   wherein each of i)-iv) is present in an amount, when combined together in the same formulation, to act synergistically to restore a level of hearing or reduce hearing loss when administered to a human subject in need thereof, wherein the molar ratio of the provitamin A carotenoid, the Vitamin C, the Vitamin E, and the magnesium compound is approximately 1:7-21:6.5-9.5:110-120,
   wherein the subject in need thereof is a subject that has already developed hearing loss caused by damage to hair cells within the inner ear associated with a ciliopathy, with age-related hearing loss, with exposure to loud noise, or an ototoxic pharmaceutical, or bacteria, or associated with a genetic mutation that upregulates production of reactive oxygen species within the cochlea, that disrupts ion exchange in the stria vascularis and Organ of Corti, or otherwise disturbs the formation or maintenance of the endolymphatic potential,
   wherein the nutraceutical formulation is encapsulated within one or more softgel or twist-off softgel capsules, or is administered orally in a non-encapsulated liquid form, and
   wherein the hearing loss is not caused by a viral infection.

16. The method of claim 1, wherein the restoration of hearing in the subject is determined by measuring increased distortion product otoacoustic emission (DPOAE) amplitude at one or more f2 frequencies chosen from 1 kHz, 1.5 kHz, 2 kHz, 3 kHz, 4 kHz, 5 kHz, 6 kHz, 7 kHz, 8 kHz, 9 kHz and 10 kHz, when compared to measured DPOAE amplitude at these same f2 frequencies prior to initial administration of the nutraceutical formulation.

17. The method of claim 14, wherein the nutraceutical formulation is administered for a duration of at least three months.

18. The method of claim 1, wherein the restoration of hearing comprises restoration of a level of hearing of at least 15%.

19. The method of claim 18, wherein the restoration of hearing comprises restoration of a level of hearing of at least 30%.

20. The method of claim 13, wherein the nutraceutical formulation is administered to a patient in an amount of 3 to 100 mg per kilogram of the patient's weight per day.

* * * * *